(12) United States Patent
Nakatsugawa et al.

(10) Patent No.: US 11,417,440 B2
(45) Date of Patent: Aug. 16, 2022

(54) RADIOGRAPHIC IMAGING APPARATUS AND METHOD OF MANUFACTURING RADIOGRAPHIC IMAGING APPARATUS

(71) Applicant: FUJIFILM Corporation, Tokyo (JP)

(72) Inventors: Haruyasu Nakatsugawa, Kanagawa (JP); Shinichi Ushikura, Kanagawa (JP); Munetaka Kato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/130,576

(22) Filed: Dec. 22, 2020

(65) Prior Publication Data

US 2021/0202125 A1 Jul. 1, 2021

(30) Foreign Application Priority Data

Dec. 27, 2019 (JP) .............................. JP2019-239568

(51) Int. Cl.
*G01J 1/58* (2006.01)
*G21K 4/00* (2006.01)
*A61B 6/00* (2006.01)
*G01T 1/20* (2006.01)

(52) U.S. Cl.
CPC ................ *G21K 4/00* (2013.01); *A61B 6/44* (2013.01); *G01T 1/20188* (2020.05); *G21K 2004/04* (2013.01); *G21K 2004/10* (2013.01); *G21K 2004/12* (2013.01)

(58) Field of Classification Search
CPC ................ G21K 4/00; G21K 2004/04; G21K 2004/10; G21K 2004/12; A61B 6/44; G01T 1/00
See application file for complete search history.

(56) References Cited

U.S. PATENT DOCUMENTS

| 2011/0198505 | A1* | 8/2011 | Ishida ..................... G01T 1/202 250/363.01 |
| 2012/0256091 | A1* | 10/2012 | Nakahashi ............ G01T 1/2018 250/361 R |
| 2018/0275287 | A1 | 9/2018 | Itaya et al. |
| 2019/0353805 | A1* | 11/2019 | Konkle ................. G01T 1/2018 |

FOREIGN PATENT DOCUMENTS

JP 2006052982 A * 8/2004
JP 2018-155699 A 10/2018

* cited by examiner

*Primary Examiner* — Kiho Kim

(74) *Attorney, Agent, or Firm* — Studebaker & Brackett PC

(57) ABSTRACT

A sensor substrate is provided with a plurality of pixels for accumulating electrical charges generated depending on light converted from radiation in a pixel region of a flexible base material. A circuit unit includes at least one of a driving substrate, a signal processing substrate, or a control substrate and is electrically connected to the sensor substrate. A fixing plate fixes the circuit unit. A conversion layer is provided on a first surface opposite to a second surface of the fixing plate on which the circuit unit is fixed, is provided in a state where the second surface opposite to the fixing plate side faces the first surface of the base material on which the pixels are provided, and converts radiation into light. A housing houses the sensor substrate, the circuit unit, the fixing plate, and the conversion layer.

11 Claims, 15 Drawing Sheets

RADIOGRAPHIC IMAGING APPARATUS AND METHOD OF MANUFACTURING RADIOGRAPHIC IMAGING APPARATUS

CROSS-REFERENCE TO RELATED APPLICATIONS

The present application claims priority under 35 U.S.C. § 119 to Japanese Patent Application No. 2019-239568 filed on Dec. 27, 2019. The above application is hereby expressly incorporated by reference, in its entirety, into the present application.

BACKGROUND

1. Technical Field

The present invention relates to a radiographic imaging apparatus and a method of manufacturing a radiographic imaging apparatus.

2. Description of the Related Art

In the related art, radiographic imaging apparatuses that perform radiographic imaging for medical diagnosis have been known. A radiation detector for detecting radiation transmitted through a subject and generating a radiographic image is used for such radiographic imaging apparatuses.

As the radiation detector, there is one comprising a conversion layer, such as a scintillator, which converts radiation into light, and a substrate in which a plurality of pixels, which accumulate electrical charges generated depending on light converted in the conversion layer, are provided. As a base material of a sensor substrate of such a radiation detector, one using a flexible base material is known (for example, refer to JP2018-155699A). Additionally, by using the flexible base material, there is a case where the weight of the radiographic imaging apparatuses can be reduced and imaging of the subject becomes easy.

SUMMARY

Meanwhile, in a case where a load, an impact, or the like is applied to a radiographic imaging apparatus, the substrate using the flexible base material is easily deflected. Therefore, in order to suppress the influence of the impact or the like on the radiation detector, the technique of increasing the bending stiffness of the radiographic imaging apparatus is known. For example, in the technique described in JP2018-155699A, a rigid plate is provided on the surface of a photoelectric conversion panel opposite to a scintillator panel side or the surface thereof on the scintillator panel side.

However, in a case where the rigid plate is provided as in the technique described in JP2018-155699A, the bending stiffness of the radiographic imaging apparatus is improved, but the weight of the entire radiographic imaging apparatus is increased.

An object of the present disclosure is to provide a radiographic imaging apparatus having high bending stiffness and reduced weight, and a method of manufacturing the radiographic imaging apparatus.

In order to achieve the above object, a radiographic imaging apparatus according to a first aspect of the present disclosure comprises a substrate in which a plurality of pixels for accumulating electrical charges generated depending on light converted from radiation is provided in a pixel region of a flexible base material; a circuit unit that is electrically connected to the substrate; a fixing plate that fixes the circuit unit; a conversion layer that is provided on a surface opposite to a surface of the fixing plate to which the circuit unit is fixed, is provided in a state where a surface opposite to the fixing plate faces a surface of the base material on which the pixels are provided, and converts the radiation into light; and a housing that houses the substrate, the circuit unit, the fixing plate, and the conversion layer.

Additionally, a radiographic imaging apparatus according to a second aspect of the present disclosure is the radiographic imaging apparatus according to the first aspect, in which an area of the fixing plate is larger than an area of the base material.

Additionally, a radiographic imaging apparatus according to a third aspect of the present disclosure is the radiographic imaging apparatus according to the first aspect, in which at least a portion of an end part of the fixing plate protrudes further outward than an end part of the base material.

Additionally, a radiographic imaging apparatus according to a fourth aspect of the present disclosure is the radiographic imaging apparatus according to the first aspect, further comprising a reinforcing substrate that is provided on a surface opposite to the surface of the base material on which the pixels are provided and has a higher stiffness than the base material.

Additionally, a radiographic imaging apparatus according to a fifth aspect of the present disclosure is the radiographic imaging apparatus according to the fourth aspect, wherein the reinforcing substrate is a top plate on a surface of the housing irradiated with the radiation.

Additionally, a radiographic imaging apparatus according to a sixth aspect of the present disclosure is the radiographic imaging apparatus according to the fourth aspect, further comprising a support member that supports an end part of the fixing plate and an end part of the reinforcing substrate.

Additionally, a radiographic imaging apparatus according to a seventh aspect of the present disclosure is the radiographic imaging apparatus according to the first aspect, further comprising a support member that supports an end part of the fixing plate and an end part of the substrate.

Additionally, a radiographic imaging apparatus according to an eighth aspect of the present disclosure is the radiographic imaging apparatus according to the first aspect, in which a space between the fixing plate and the substrate is sealed with a sealing member.

Additionally, a radiographic imaging apparatus according to a ninth aspect of the present disclosure is the radiographic imaging apparatus according to the first aspect, further comprising a pressure sensitive adhesive layer for providing the conversion layer on the surface of the base material on which the pixels are provided.

Additionally, a radiographic imaging apparatus according to a tenth aspect of the present disclosure is the radiographic imaging apparatus according to the first aspect, in which a surface of the conversion layer opposite to the fixing plate and the surface of the base material on which the pixels are provided are in contact with each other.

Additionally, a radiographic imaging apparatus according to an eleventh aspect of the present disclosure is the radiographic imaging apparatus according to the first aspect, in which a main component of a material of the fixing plate is carbon.

Additionally, a radiographic imaging apparatus according to a twelfth aspect of the present disclosure is the radiographic imaging apparatus according to the first aspect, in which the housing houses the substrate, the conversion layer, the fixing plate, and the circuit unit in an arrangement order in order from a side irradiated with the radiation.

Additionally, a method of manufacturing a radiographic imaging apparatus according to a thirteenth aspect of the present disclosure comprises a step of providing a flexible base material on a support body and forming a substrate in which a plurality of pixels for accumulating electrical charges generated depending on light converted from radiation is provided in a pixel region of the base material; a step of forming a conversion layer that converts the radiation into light on a fixing plate for fixing a circuit unit electrically connected to the substrate; a step of providing the conversion layer on the substrate by making a surface of the base material on which the pixels are provided face a surface of the conversion layer opposite to the fixing plate; and a step of peeling the substrate provided with the conversion layer from the support body; and a step of fixing the circuit unit to a surface of the fixing plate opposite to a side where the conversion layer is formed.

Additionally, a method of manufacturing a radiographic imaging apparatus according to a fourteenth aspect of the present disclosure is the method of manufacturing a radiographic imaging apparatus according to the thirteenth aspect, further comprising, before the step of peeling the substrate from the support body, a step of connecting one end of a flexible cable connected to the circuit unit to the substrate; and a step of fixing the flexible cable to the fixing plate.

Additionally, a method of manufacturing a radiographic imaging apparatus according to a fifteenth aspect of the present disclosure is the method of manufacturing a radiographic imaging apparatus according to the thirteenth aspect, in which the conversion layer is formed by depositing a phosphor by a vapor deposition method using the fixing plate as a substrate.

Additionally, a method of manufacturing a radiographic imaging apparatus according to a sixteenth aspect of the present disclosure is the method of manufacturing a radiographic imaging apparatus according to the thirteenth aspect, in which the conversion layer is formed by applying a resin, in which a phosphor is dispersed, to the fixing plate.

According to the present disclosure, it is possible to increase bending stiffness and reduce weight.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the present invention will be described in detail with reference to the drawings. In addition, the present embodiments do not limit the present invention.

A radiation detector of the present embodiment has a function of detecting radiation transmitted through a subject and outputting image information representing a radiographic image of the subject. The radiation detector of the present embodiment comprises a sensor substrate and a conversion layer that converts radiation into light (refer to a sensor substrate 12 and a conversion layer 14 of the radiation detector 10 in FIG. 2). The sensor substrate 12 of the present embodiment is an example of a substrate of the present disclosure.

Figure 1:
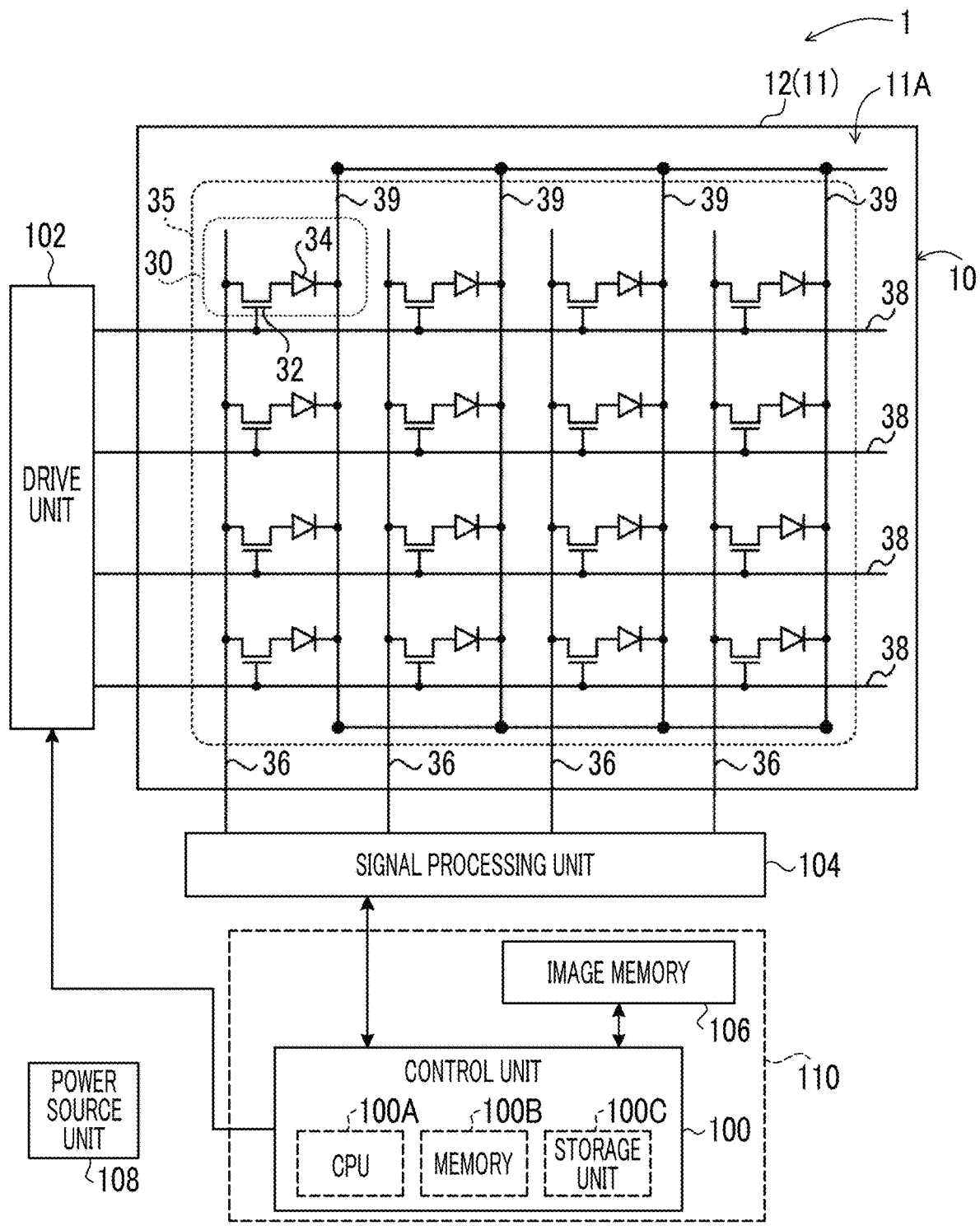
FIG. 1 is a block diagram illustrating an example of the configuration of main parts of an electrical system in a radiographic imaging apparatus of an embodiment.

First, the outline of an example of the configuration of an electrical system in a radiographic imaging apparatus of the present embodiment will be described with reference to FIG. 1. FIG. 1 is a block diagram illustrating an example of the configuration of main parts of the electrical system in the radiographic imaging apparatus of the present embodiment.

As illustrated in FIG. 1, the radiographic imaging apparatus 1 of the present embodiment comprises the radiation detector 10, a control unit 100, a drive unit 102, a signal processing unit 104, an image memory 106, and a power source unit 108.

The radiation detector 10 comprises a sensor substrate 12 and a conversion layer (refer to FIG. 2) that converts radiation into light. The sensor substrate 12 comprises a flexible base material 11, and a plurality of pixels 30 provided on a first surface 11A of the base material 11. In addition, in the following, the plurality of pixels 30 may be simply referred to as "pixels 30". The first surface 11A in the present embodiment is an example of a surface of the base material on which pixels are provided in the present disclosure. Additionally, a second surface 11B of the base material 11 opposite to the first surface 11A in the present embodiment is an example of a surface opposite to the surface of the base material on which the pixels are provided in the present disclosure.

As illustrated in FIG. 1, each pixel 30 of the present embodiment comprises a sensor unit 34 that generates and accumulates electrical charges depending on the light converted by the conversion layer, and a switching element 32 that reads out the electrical charges accumulated in the sensor unit 34. In the present embodiment, as an example, a thin film transistor (TFT) is used as the switching element 32. For that reason, in the following description, the switching element 32 is referred to as a "TFT 32". In the present embodiment, a layer in which the pixels 30 are formed on the first surface 11A of the base material 11 is provided as a layer that is formed with the sensor unit 34 and the TFT 32 and is planarized.

The pixels 30 are two-dimensionally arranged in one direction (a scanning wiring direction corresponding to a transverse direction of FIG. 1, hereinafter referred to as a "row direction"), and a direction intersecting the row direction (a signal wiring direction corresponding to the machine direction of FIG. 1, hereinafter referred as a "column direction") in a pixel region 35 of the sensor substrate 12. Although an array of the pixels 30 is illustrated in a simplified manner in FIG. 1, for example, 1024×1024 pixels 30 are arranged in the row direction and the column direction.

Additionally, a plurality of scanning wiring lines 38, which are provided for respective rows of the pixels 30 to control switching states (ON and OFF) of the TFTs 32, and a plurality of signal wiring lines 36, which are provided for respective columns of the pixels 30 and from which electrical charges accumulated in the sensor units 34 are read, are provided in a mutually intersecting manner in the radiation detector 10. Each of the plurality of scanning wiring lines 38 is connected to the drive unit 102 via a flexible cable 112A (refer to FIG. 2), and thereby, a drive signal for driving the TFT 32 output from the drive unit 102 to control the switching state thereof flows through each of the plurality of scanning wiring lines 38. Additionally, the plurality of signal wiring lines 36 are electrically connected to the signal processing unit 104 via the flexible cable 112B (refer to FIG. 2), respectively, and thereby, electrical charges read from the respective pixels 30 are output to the signal processing unit 104 as electrical signals. The signal processing unit 104 generates and outputs image data according to the input electrical signals. In addition, in the present embodiment, the term "connection" with respect to the flexible cable 112 means an electrical connection.

The control unit 100 to be described below is connected to the signal processing unit 104, and the image data output from the signal processing unit 104 is sequentially output to the control unit 100. The image memory 106 is connected to the control unit 100, and the image data sequentially output from the signal processing unit 104 is sequentially stored in the image memory 106 under the control of the control unit 100. The image memory 106 has a storage capacity capable of storing image data equivalent to a predetermined number of sheets, and whenever radiographic images are captured, image data obtained by the capturing is sequentially stored in the image memory 106.

The control unit 100 comprises a central processing unit (CPU) 100A, a memory 100B including a read only memory (ROM), a random access memory (RAM), and the like, and a nonvolatile storage unit 100C, such as a flash memory. An example of the control unit 100 is a microcomputer or the like. The control unit 100 controls the overall operation of the radiographic imaging apparatus 1.

In addition, in the radiographic imaging apparatus 1 of the present embodiment, the image memory 106, the control unit 100, and the like are formed in a control substrate 110.

Additionally, common wiring lines 39 are provided in a wiring direction of the signal wiring lines 36 at the sensor units 34 of the respective pixels 30 in order to apply bias voltages to the respective pixels 30. Bias voltages are applied to the respective pixels 30 from a bias power source by electrically connecting the common wiring lines 39 to the bias power source (not illustrated) outside the sensor substrate 12.

The power source unit 108 supplies electrical power to various elements and various circuits, such as the control unit 100, the drive unit 102, the signal processing unit 104, the image memory 106, and the power source unit 108. In addition, in FIG. 1, an illustration of wiring lines, which connect the power source unit 108 and various elements or various circuits together, is omitted in order to avoid complications.

Figure 2:
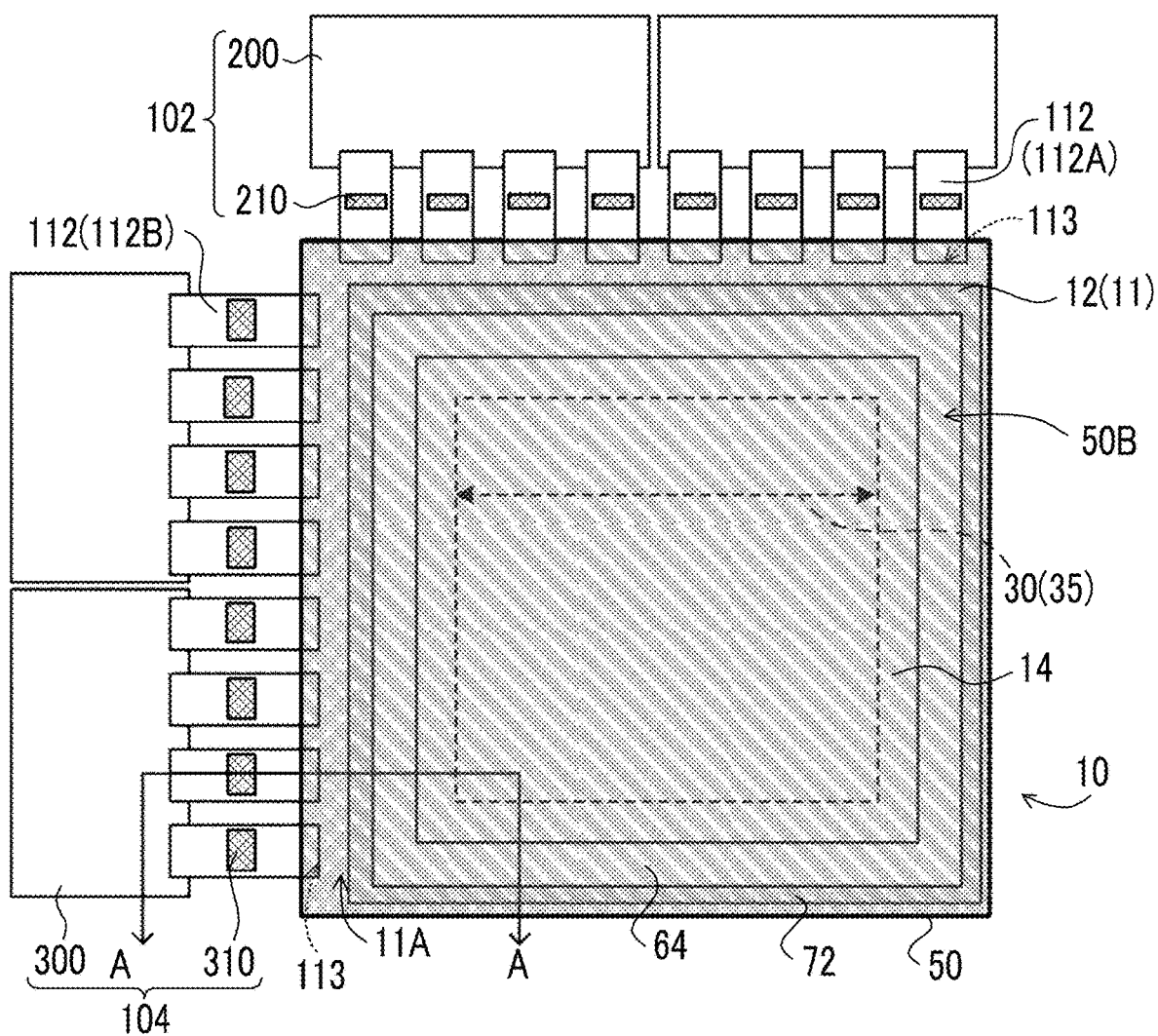
FIG. 2 is a plan view of an example of a radiation detector according to the embodiment as seen from a first surface side of a base material.
Figure 3:
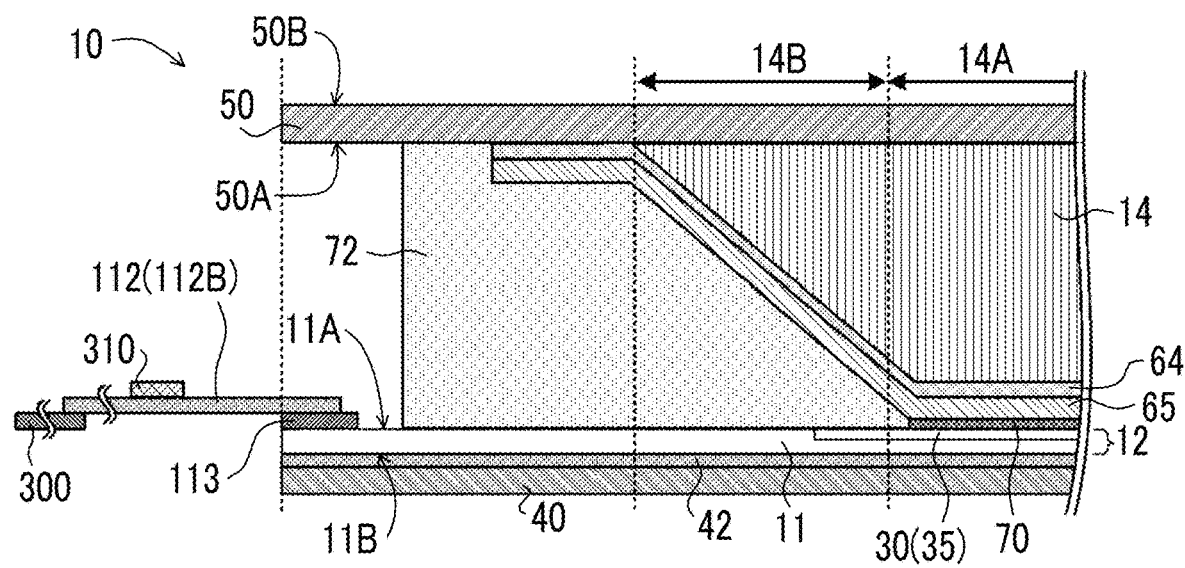
FIG. 3 is a cross-sectional view taken along line A-A of the radiation detector illustrated in FIG. 2.

Moreover, the radiation detector 10 will be described in detail. FIG. 2 is an example of a plan view of the radiation detector 10 according to the present embodiment as seen from the first surface 11A side of the base material 11. Additionally, FIG. 3 is an example of a cross-sectional view taken along line A-A of the radiation detector 10 in FIG. 2.

The base material 11 is a resin sheet that has flexibility and includes, for example, a plastic such as a polyimide (PI). The thickness of the base material 11 may be a thickness such that desired flexibility is obtained depending on the hardness of a material, the size of the sensor substrate 12, that is, the area of the first surface 11A or the second surface 11B, and the like. In the case of a rectangular base material 11 alone, an example having flexibility indicates one in which the base material 11 hangs down (becomes lower than the height of the fixed side) 2 mm or more due to the gravity of the base material 11 resulting from its own weight at a position 10 cm away from the fixed side with one side of the base material 11 fixed. As a specific example in a case where the base material 11 is the resin sheet, the thickness thereof may be 5 µm to 125 µm, and the thickness thereof may be more preferably 20 µm to 50 µm.

In addition, the base material 11 has characteristics capable of withstanding the manufacture of the pixels 30 and has characteristics capable of withstanding the manufacture of amorphous silicon TFT (a-Si TFT) in the present embodiment. As such a characteristic of the base material 11, it is preferable that the coefficient of thermal expansion (CTE) at 300° C. to 400° C. is about the same as that of amorphous silicon (Si) wafer (for example, ±5 ppm/K), specifically, the amount is preferably 20 ppm/K or less. Additionally, as the heat shrinkage rate of the base material 11, it is preferable that the heat shrinkage rate at 400° C. is 0.5% or less with the thickness being 25 µm. Additionally, it is preferable that the modulus of elasticity of the base material 11 does not have a transition point that general PI has, in a temperature region of 300° C. to 400° C., and the modulus of elasticity at 500° C. is 1 GPa or more.

Additionally, it is preferable that the base material 11 of the present embodiment has a fine particle layer containing inorganic fine particles having an average particle diameter of 0.05 µm or more and 2.5 µm or less, which absorbs backscattered radiation by itself in order to suppress backscattered radiation. In addition, as the inorganic fine particles, in the case of the resinous base material 11, it is preferable to use an inorganic material of which the atomic number is larger than the atoms constituting the organic material that is the base material 11 and is 30 or less. Specific examples of such fine particles include $SiO_2$ that is an oxide of Si having an atomic number of 14, MgO that is an oxide of Mg having an atomic number of 12, $Al_2O_3$ that is an oxide of Al having an atomic number of 13, $TiO_2$ that is an oxide of Ti having an atomic number of 22, and the like. A specific example of the resin sheet having such characteristics is XENOMAX (registered trademark).

In addition, the above thicknesses in the present embodiment were measured using a micrometer. The coefficient of thermal expansion was measured according to JIS K7197: 1991. In addition, the measurement was performed by cutting out test pieces from a main surface of the base material 11 while changing the angle by 15 degrees, measuring the coefficient of thermal expansion of each of the cut-out test pieces, and setting the highest value as the coefficient of thermal expansion of the base material 11. The coefficient of thermal expansion is measured at intervals of 10° C. between −50° C. and 450° C. in a machine direction (MD) and a transverse direction (TD), and (ppm/° C.) is converted to (ppm/K). For the measurement of the coefficient of thermal expansion, the TMA4000S device made by MAC Science Co., Ltd. is used, sample length is 10 mm, sample width is 2 mm, initial load is 34.5 g/mm$^2$, temperature rising rate is 5° C./min, and the atmosphere is in argon.

The base material 11 having desired flexibility is not limited to a resinous material such as the resin sheet. For example, the base material 11 may be a glass substrate or the like having a relatively small thickness. As a specific example of a case where the base material 11 is the glass substrate, generally, in a size of about 43 cm on a side, the glass substrate has flexibility as long as the thickness is 0.3 mm or less. Therefore, any desired glass substrate may be used as long as the thickness is 0.3 mm or less.

As illustrated in FIGS. 2 and 3, the plurality of pixels 30 are provided on the first surface 11A of the base material 11. In the present embodiment, a region on the first surface 11A of the base material 11 where the pixels 30 are provided is the pixel region 35.

Additionally, the conversion layer 14 is provided on the first surface 11A of the base material 11 by the pressure sensitive adhesive layer 70. The conversion layer 14 includes a phosphor and has a function of converting radiation into light. In the present embodiment, a scintillator including CsI (cesium iodide) as a phosphor is used as an example of the conversion layer 14. It is preferable that such a scintillator includes, for example, CsI:Tl (cesium iodide to which thallium is added) or CsI:Na (cesium iodide to which sodium is added) having an emission spectrum of 400 nm to 700 nm in the case of X-ray radiation. In addition, the emission peak wavelength in a visible light region of CsI:Tl is 565 nm.

The conversion layer 14 of the present embodiment is directly formed on a first surface 50A of a fixing plate 50 provided opposite to the base material 11 side. For example, in a case where the conversion layer 14 is the scintillator containing CsI as described above, the conversion layer 14 is directly formed on the fixing plate 50 by the vapor deposition method using the fixing plate 50 as a substrate. Additionally, unlike the present embodiment, for example, in a case where the conversion layer 14 is a scintillator containing a phosphor such as GOS ($Gd_2O_2S$:Tb), the conversion layer 14 is directly formed on the fixing plate 50 by applying a binder, such as a resin in which the phosphor is dispersed, to the fixing plate 50. In addition, the conversion efficiency from radiation to visible light is higher in a case where CsI is used for the conversion layer 14 than in a case where GOS is used.

The fixing plate 50 is a base for supporting a driving substrate 200, a signal processing substrate 300, and the control substrate 110. At least one of the driving substrate 200, the signal processing substrate 300, or the control substrate 110 of the present embodiment is an example of a circuit unit of the present disclosure. Hereinafter, the driving substrate 200, the signal processing substrate 300, and the control substrate 110 are collectively referred to as the "circuit unit". Specifically, each of the driving substrate 200, the signal processing substrate 300, and the control substrate 110, which are connected to the pixels 30 by the flexible cable 112, is fixed to a second surface 50B of the fixing plate 50 (also refer to FIG. 4). As materials of the fixing plate 50, for example, a metal containing at least one of Mg, Al, and Li, carbon, or the like are preferable, and a material containing carbon as a main component is more preferable.

From the viewpoint of supporting the circuit unit, the fixing plate 50 preferably has high bending stiffness and has higher bending stiffness than at least the base material 11. In addition, in a case where the bending modulus of elasticity decreases, the bending stiffness also decreases. In order to obtain a desired bending stiffness, the thickness of the fixing plate 50 should be increased, and the thickness of the radiation detector 10 as a whole increases. Considering the appropriate stiffness and the thickness of the radiation detector 10 as a whole, it is preferable that the material used for the fixing plate 50 has a bending modulus of elasticity of 1000 MPa or more and 40,000 MPa or less. Additionally, the bending stiffness of the fixing plate 50 is preferably 36,000 Pacm$^4$ or more and 2,240,000 Pacm$^4$ or less.

Additionally, the thickness of the fixing plate 50 may be any thickness as long as the above-described desired bending modulus of elasticity and bending stiffness are obtained.

However, in consideration of the thickness of the radiation detector 10 as a whole, it is preferable that the thickness of the fixing plate 50 is 0.1 mm or more and of 0.25 mm or less. Additionally, as an example, the size of the fixing plate 50 of the present embodiment, specifically, the area of the first surface 50A facing the first surface 11A of the base material 11 is the same as the first surface 11A of the base material 11. In addition, in the present embodiment, the "same" mean being the same, including a range that can be regarded as an error.

As illustrated in FIG. 3, the conversion layer 14 of the present embodiment is formed with an inclination such that the thickness thereof gradually decreases toward an outer edge thereof. In the following, a central region of the conversion layer 14 where the thickness in a case where manufacturing errors and measurement errors are neglected can be considered to be substantially constant is referred to as a central part 14A. Additionally, an outer peripheral region of the conversion layer 14 having a thickness of, for example, 90% or less of the average thickness of the central part 14A of the conversion layer 14 is referred to as a peripheral edge part 14B. That is, the conversion layer 14 has an inclined surface that is inclined with respect to the fixing plate 50 at the peripheral edge part 14B. In addition, in the following, for convenience of description, in a case where "upper" or "lower" are mentioned with the conversion layer 14 as a reference, a side in contact with the fixing plate 50 is referred to as "lower", and a side facing the sensor substrate 12 is referred to as "upper". For example, the inclined surface of the peripheral edge part 14B of the conversion layer 14 is inclined in a state where the conversion layer 14 gradually expands from the upper side to the lower side.

Additionally, as illustrated in FIG. 3, an adhesive layer 64 and a protective layer 65 are provided on the conversion layer 14 of the present embodiment.

The adhesive layer 64 covers the entire surface of the conversion layer 14. An end part of the adhesive layer 64 extends to the first surface 50A of the fixing plate 50. That is, the adhesive layer 64 adheres to the fixing plate 50 at an end part thereof. The adhesive layer 64 has a function of fixing the protective layer 65 to the conversion layer 14. The adhesive layer 64 preferably has optical transparency. As materials of the adhesive layer 64, for example, an acrylic pressure sensitive adhesive, a hot melt pressure sensitive adhesive, and a silicone adhesive can be used. Examples of the acrylic pressure sensitive adhesive include urethane acrylate, acrylic resin acrylate, epoxy acrylate, and the like. Examples of the hot-melt pressure sensitive adhesive include thermoplastics, such as ethylene-vinyl acetate copolymer resin (EVA), ethylene-acrylate copolymer resin (EAA), ethylene-ethyl acrylate copolymer resin (EEA), and ethylene-methyl methacrylate copolymer (EMMA). The thickness of the adhesive layer 64 is preferably 2 µm or more and 7 µm or less. By setting the thickness of the adhesive layer 64 to 2 µm or more, the effect of fixing the protective layer 65 on the conversion layer 14 can be sufficiently exhibited. Additionally, by setting the thickness of the adhesive layer 64 to 7 µm or less, it is possible to suppress a decrease in modulation transfer function (MTF) and detective quantum efficiency (DQE).

The protective layer 65 is provided so as to cover the entire conversion layer 14 and covers a part of the first surface 50A of the fixing plate 50 at the end part thereof. The protective layer 65 functions as a moistureproof film that prevents moisture from entering the conversion layer 14. As the material of the protective layer 65, for example, organic films containing organic materials such as polyethylene terephthalate (PET), polyphenylene sulfide (PPS), oriented polypropylene (OPP: biaxially oriented polypropylene film), polyethylene naphthalate (PEN), and PI, and Parylene (registered trademark) can be used. Additionally, as the protective layer 65, a laminated film of a resin film and a metal film may be used. Examples of the laminated film of the resin film and the metal film include ALPET (registered trademark) sheets.

Additionally, as illustrated in FIG. 3, the space between the sensor substrate 12 and the fixing plate 50 is sealed by a sealing member 72. Specifically, the sealing member 72 is provided in a space formed by the conversion layer 14 (protective layer 65), the sensor substrate 12, and the fixing plate 50 in a region corresponding to the peripheral edge part 14B of the conversion layer 14 and a region further outside thereof between the sensor substrate 12 and the fixing plate 50. Additionally, as illustrated in FIG. 3, the sealing member 72 is not provided on a terminal 113 and the flexible cable 112. The material of the sealing member 72 is not particularly limited, and for example, resin can be used. In this way, by filling the space formed between the sensor substrate 12 and the fixing plate 50 with the sealing member 72, the bending stiffness of the radiation detector 10 can be increased. Additionally, it is possible to inhibit the conversion layer 14 from being peeled off from the sensor substrate 12.

Additionally, as illustrated in FIG. 3, a reinforcing substrate 40 is provided on the second surface 11B side of the base material 11 via a pressure sensitive adhesive 42 in the sensor substrate 12 of the radiation detector 10 of the present embodiment.

The reinforcing substrate 40 has a function of reinforcing the strength of the base material 11. The reinforcing substrate 40 of the present embodiment is higher in bending stiffness than the base material 11, and the dimensional change (deformation) thereof with respect to a force applied in a direction perpendicular to the surface opposite to the conversion layer 14 is smaller than the dimensional change (deformation) thereof with respect to a force applied in the direction perpendicular to the second surface 11B of the base material 11. Examples of the material of the reinforcing substrate 40 include carbon, plastic, and the like. In addition, the reinforcing substrate 40 may include a plurality of materials or may be, for example, a laminate of plastic and carbon.

In addition, specifically, the bending stiffness of the reinforcing substrate 40 is preferably 100 times or more the bending stiffness of the base material 11. Additionally, the thickness of the reinforcing substrate 40 of the present embodiment is larger than the thickness of the base material 11. For example, in a case where XENOMAX (registered trademark) is used as the base material 11, the thickness of the reinforcing substrate 40 is preferably about 0.2 mm to 0.25 mm.

Specifically, a material having a bending modulus of elasticity of 150 MPa or more and 2,500 MPa or less is preferably used for the reinforcing substrate 40 of the present embodiment. From the viewpoint of suppressing the deflection of the base material 11, the reinforcing substrate 40 preferably has a higher bending stiffness than the base material 11. In addition, in a case where the bending modulus of elasticity becomes low, the bending stiffness also becomes low. In order to obtain a desired bending stiffness, the thickness of the reinforcing substrate 40 should be made large, and the thickness of the entire radiation detector 10 increases. Considering the above-described material of the reinforcing substrate 40, the thickness of the reinforcing substrate 40 tends to be relatively large in a case where a bending stiffness exceeding 140,000 Pacm$^4$ is to be obtained. For that reason, in view of obtaining appropriate stiffness and considering the thickness of the entire radiation detector 10, the material used for the reinforcing substrate 40 preferably has a bending modulus of elasticity of 150 MPa or more and 2,500 MPa or less. Additionally, the bending stiffness of the reinforcing substrate 40 is preferably 540 Pacm$^4$ or more and 140,000 Pacm$^4$ or less.

Additionally, the coefficient of thermal expansion of the reinforcing substrate 40 of the present embodiment is preferably closer to the coefficient of thermal expansion of the material of the conversion layer 14, and more preferably the ratio of the coefficient of thermal expansion of the reinforcing substrate 40 to the coefficient of thermal expansion of the conversion layer 14 (the coefficient of thermal expansion of the reinforcing substrate 40/the coefficient of thermal expansion of the conversion layer 14) is more preferably 0.5 or more and 2 or less. The coefficient of thermal expansion of such a reinforcing substrate 40 is preferably 30 ppm/K or more and 80 ppm/K or less. For example, in a case where the conversion layer 14 has CsI:Tl as a material, the coefficient of thermal expansion is 50 ppm/K. In this case, examples of materials relatively close to the conversion layer 14 include polyvinyl chloride (PVC) having a coefficient of thermal expansion of 60 ppm/K to 80 ppm/K, acrylic having a coefficient of thermal expansion of 70 ppm/K to 80 ppm/K, PET having a coefficient of thermal expansion of 65 ppm/K to 70 ppm/K, polycarbonate (PC) having a coefficient of thermal expansion of 65 ppm/K, Teflon (registered trademark) having a coefficient of thermal expansion of 45 ppm/K to 70 ppm/K, and the like. Moreover, considering the above-described bending modulus of elasticity, the material of the reinforcing substrate 40 is more preferably a material containing at least one of PET or PC.

From the viewpoint of elasticity, the reinforcing substrate 40 preferably contains a material having a yield point. In addition, in the present embodiment, the "yield point" means a phenomenon in which the stress rapidly decreases once in a case where the material is pulled, means that the strain is increased without increasing the stress on a curve representing a relationship between the stress and the strain, and indicates the peak of a stress-strain curve in a case where a tensile strength test is performed on the material. Resins having the yield point generally include resins that are hard and strongly sticky, and resins that are soft and strongly sticky and have medium strength. Examples of the hard and strongly sticky resins include PC and the like. Additionally, examples of the resins that are soft and strongly sticky and have medium strength include polypropylene and the like.

In a case where the reinforcing substrate 40 of the present embodiment is a substrate having plastic as a material, the material is preferably a thermoplastic resin for the above-described reasons, and include at least one of PC, PET, styrene, acrylic, polyacetase, nylon, polypropylene, acrylonitrile butadiene styrene (ABS), engineering plastics, or polyphenylene ether. In addition, the reinforcing substrate 40 is preferably at least one of polypropylene, ABS, engineering plastics, PET, or polyphenylene ether among these, is more preferably at least one of styrene, acrylics, polyacetase, or nylon, and is more preferably at least one of PC or PET.

Meanwhile, as illustrated in FIG. 2, a plurality (16 in FIG. 2) of the terminals 113 are provided on an outer edge part of the base material 11. An anisotropic conductive film or the like is used as the terminals 113. As illustrated in FIGS. 2 and 3, the flexible cable 112 is electrically connected to each of the plurality of terminals 113. Specifically, as illustrated in FIG. 2, the flexible cable 112A is thermocompression bonded to each of the plurality of (eight in FIG. 2) terminals 113 provided on one side of the base material 11. The flexible cable 112A is a so-called chip on film (COF), and a driving integrated circuit (IC) 210 is mounted on the flexible cable 112A. The driving IC 210 is connected to each of a plurality of signal lines included in the flexible cable 112A. In addition, in the present embodiment, the flexible cable 112A and the flexible cable 112B to be described below are simply referred to as "flexible cable 112" in a case where the cables are collectively referred to without distinction.

The other end of the flexible cable 112A opposite to the one end electrically connected to the terminal 113 of the sensor substrate 12 is electrically connected to the driving substrate 200. As an example, in the present embodiment, the plurality of signal lines included in the flexible cable 112A are thermocompression bonded to the driving substrate 200 and thereby electrically connect to circuits and elements (not illustrated) mounted on the driving substrate 200. In addition, the method of electrically connecting the driving substrate 200 and the flexible cable 112A is not limited to the present embodiment. For example, a configuration may be adopted in which the driving substrate 200 and the flexible cable 112A are electrically connected by a connector. Examples of such a connector include a zero insertion force (ZIF) structure connector and a Non-ZIF structure connector.

The driving substrate 200 of the present embodiment is a flexible printed circuit board (PCB), which is a so-called flexible substrate. Additionally, circuit components (not illustrated) mounted on the driving substrate 200 are components mainly used for processing digital signals (hereinafter, referred to as "digital components"). Digital components tend to have a relatively smaller area (size) than analog components to be described below. Specific examples of the digital components include digital buffers, bypass capacitors, pull-up/pull-down resistors, damping resistors, electromagnetic compatibility (EMC) countermeasure chip components, power source ICs, and the like. In addition, the driving substrate 200 may be not necessarily a flexible substrate and may be an inflexible rigid substrate or a rigid flexible substrate.

In the present embodiment, the drive unit 102 is realized by the driving substrate 200 and the driving IC 210 mounted on the flexible cable 112A. In addition, the driving IC 210 includes, among various circuits and elements that realize the drive unit 102, circuits different from the digital components mounted on the driving substrate 200.

Meanwhile, the flexible cable 112B is electrically connected to each of the plurality (8 in FIG. 2) of terminals 113 provided on a side intersecting with one side of the base material 11 to which the flexible cable 112A is electrically connected. Similarly the flexible cable 112A, the flexible cable 112B is a so-called chip on film (COF), and a signal processing IC 310 is mounted on the flexible cable 112B. The signal processing IC 310 is connected to a plurality of signal lines (not illustrated) included in the flexible cable 112B.

The other end of the flexible cable 112B opposite to one end electrically connected to the terminal 113 of the sensor substrate 12 is electrically connected to the signal processing substrate 300. As an example, in the present embodiment, the plurality of signal lines included in the flexible cable 112B are thermocompression bonded to the signal processing substrate 300 and thereby connected to the circuits and elements (not illustrated) mounted on the signal processing substrate 300. In addition, the method of electrically connecting the signal processing substrate 300 and the flexible cable 112B is not limited to the present embodiment. For example, a configuration may be adopted in which the signal processing substrate 300 and the flexible cable 112B are electrically connected by a connector. Examples of such a connector include a zero insertion force (ZIF) structure connector and a Non-ZIF structure connector. Additionally, the method of electrically connecting the flexible cable 112A and the driving substrate 200 and the method of electrically connecting the flexible cable 112B and the signal processing substrate 300 may be the same or different. For example, a configuration may be adopted in which the flexible cable 112A and the driving substrate 200 are electrically connected by thermocompression bonding, and the flexible cable 112B and the signal processing substrate 300 are electrically connected by a connector.

The signal processing substrate 300 of the present embodiment is a flexible PCB, which is a so-called flexible substrate, similarly to the above-described driving substrate 200. Circuit components (not illustrated) mounted on the signal processing substrate 300 are components mainly used for processing analog signals (hereinafter referred to as "analog components"). Specific examples of the analog components include charge amplifiers, analog-digital converters (ADCs), digital-analog converters (DAC), and power source ICs. Additionally, the circuit components of the present embodiment also include coils around a power source, which has a relatively large component size, and smoothing large-capacity capacitors. In addition, the signal processing substrate 300 may not necessarily a flexible substrate and may be an inflexible rigid substrate or a rigid flexible substrate.

In the present embodiment, the signal processing unit 104 is realized by the signal processing substrate 300 and the signal processing IC 310 mounted on the flexible cable 112B. In addition, the signal processing IC 310 includes, among various circuits and elements that realize the signal processing unit 104, circuits different from the analog components mounted on the signal processing substrate 300.

In addition, in FIG. 2, a configuration in which a plurality of (two) the driving substrates 200 and a plurality of (two) the signal processing substrates 300 are provided has been described. However, the number of driving substrates 200 and the number of signal processing substrates 300 are not limited to those illustrated in FIG. 2. For example, a configuration may be adopted in which at least one of the driving substrate 200 or the signal processing substrate 300 may be a single substrate.

Meanwhile, as illustrated in FIG. 3, in the radiation detector 10 of the present embodiment, the flexible cable 112 is thermocompression bonded to the terminal 113, and thereby the flexible cable 112 is electrically connected to the terminal 113. In addition, although FIG. 3 is a view illustrating an example of a structure relating to the electrical connection between the flexible cable 112B and the radiation detector 10, a structure related to the electrical connection between the flexible cable 112A and the radiation detector 10 of the present embodiment is also the same as the configuration illustrated in FIG. 3.

Figure 4:
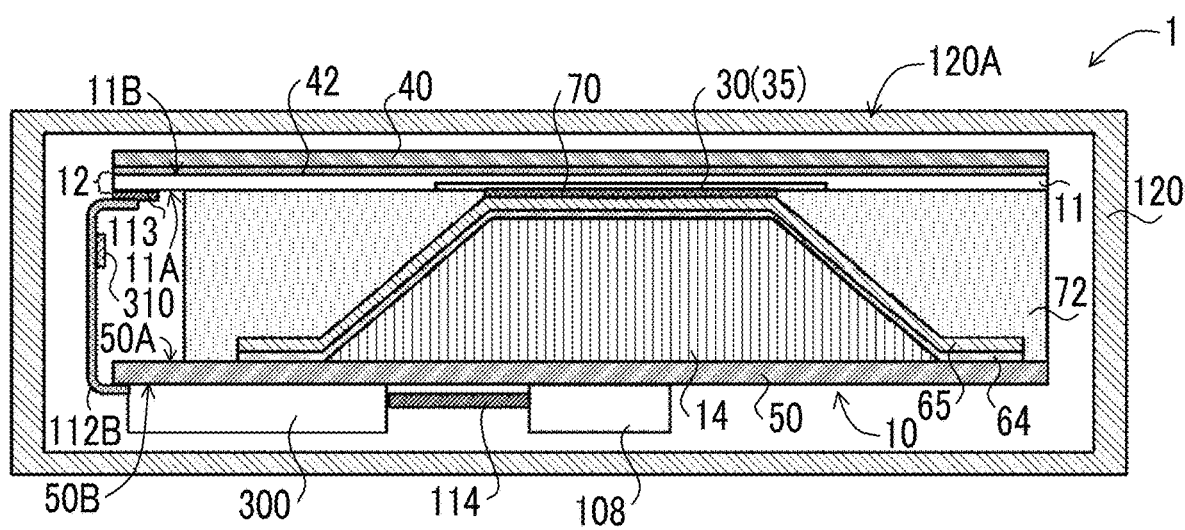
FIG. 4 is a cross-sectional view of an example of the radiographic imaging apparatus according to the embodiment.

Moreover, the radiographic imaging apparatus 1 will be described in detail. FIG. 4 is an example of a cross-sectional view of the radiographic imaging apparatus 1 of the present embodiment. The radiographic imaging apparatus 1 of the present embodiment is an irradiation side sampling (ISS) type radiographic imaging apparatus in which radiation is emitted from the second surface 11B side of the base material 11.

The radiographic imaging apparatus 1 using the above radiation detector 10 is used while being housed in a housing 120, as illustrated in FIG. 4. As illustrated in FIG. 4, the radiation detector 10, the power source unit 108, and the control substrate 110 (not illustrated in FIG. 4) are provided side by side in a direction intersecting an incidence direction of radiation within the housing 120. The radiation detector 10 is disposed in a state where the second surface 11B of the base material 11 faces a top plate on an irradiation surface 120A side of the housing 120 that is irradiated with the radiation transmitted through a subject. More specifically, the reinforcing substrate 40 provided on the second surface 11B of the base material 11 of the sensor substrate 12 is disposed to face the top plate on the irradiation surface 120A side of the housing 120.

As described above, the signal processing substrate 300 electrically connected to the sensor substrate 12 by the flexible cable 112B is fixed to the second surface 50B of the fixing plate 50. Additionally, although not illustrated in FIG. 4C, the driving substrate 200 electrically connected to the sensor substrate 12 by the flexible cable 112A is also fixed to the second surface 50B of the fixing plate 50. Moreover, the control substrate 110 electrically connected to the driving substrate 200 and the signal processing substrate 300 is also fixed to the second surface 50B of the fixing plate 50.

Each of the signal processing substrate 300, the driving substrate 200, and the control substrate 110 is connected to the power source unit 108 by a power source line 114.

The housing 120 is preferably lightweight, has a low absorbance of radiation, particularly X-rays, and has a high stiffness, and is preferably made of a material having a sufficiently high modulus of elasticity. As the material of the housing 120, it is preferable to use a material having a bending modulus of elasticity of 10,000 MPa or more. As the material of the housing 120, carbon or carbon fiber reinforced plastics (CFRP) having a bending modulus of elasticity of about 20,000 to 60,000 MPa can be suitably used.

In the capturing of a radiographic image by the radiographic imaging apparatus 1, a load from a subject is applied to the irradiation surface 120A of the housing 120. In a case where the stiffness of the housing 120 is insufficient, there are concerns that problems may occur such that the sensor substrate 12 is deflected due to the load from the subject and the pixels 30 are damaged. By housing the radiation detector 10 inside the housing 120 made of a material having a bending modulus of elasticity of 10,000 MPa or more, it is possible to suppress the deflection of the sensor substrate 12 due to the load from the subject.

In addition, the housing 120 may be formed of different materials for the irradiation surface 120A of the housing 120 and other portions. For example, a portion corresponding to the irradiation surface 120A may be formed of a material having a low radiation absorbance and high stiffness and having a sufficiently high modulus of elasticity, and the other portions may be formed of a material different from the portion corresponding to the irradiation surface 120A, for example, a material having a lower modulus of elasticity than the portion of the irradiation surface 120A.

A method of manufacturing the radiographic imaging apparatus 1 according to the present embodiment will be described with reference to FIGS. 5A to 5G.

Figure 5A:
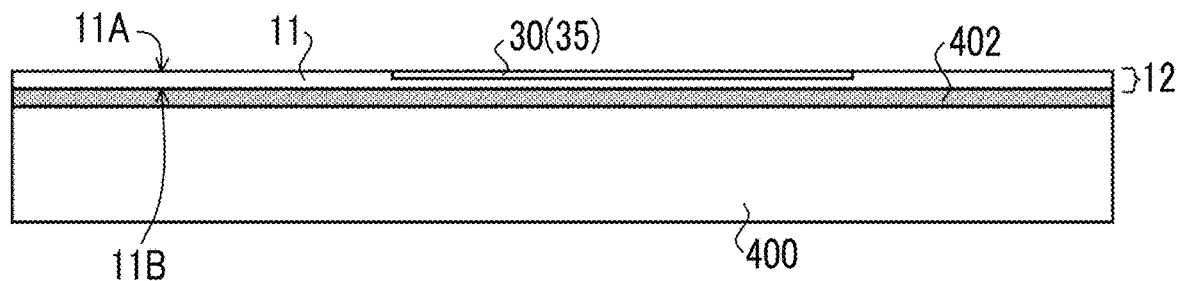
FIG. 5A is a view for explaining an example of a method of manufacturing the radiographic imaging apparatus of the embodiment.

As illustrated in FIG. 5A, the base material 11 is formed on a support body 400, such as a glass substrate having a thickness larger than that of the base material 11, via a peeling layer 402, for example in order to form the sensor substrate 12. For example, in a case where the base material 11 is formed by a lamination method, a sheet to be the base material 11 is bonded onto the support body 400. The second surface 11B of the base material 11 is in contact with the peeling layer 402. In addition, the method of forming the base material 11 is not limited to the present embodiment. For example, a configuration may be adopted in which the base material 11 is formed by an application method.

Moreover, the pixels 30 are formed in the pixel region 35 on the first surface 11A of the base material 11. In addition, in the present embodiment, as an example, the pixels 30 are formed on the first surface 11A of the base material 11 via an undercoat (not illustrated) made of SiN or the like.

Figure 5B:
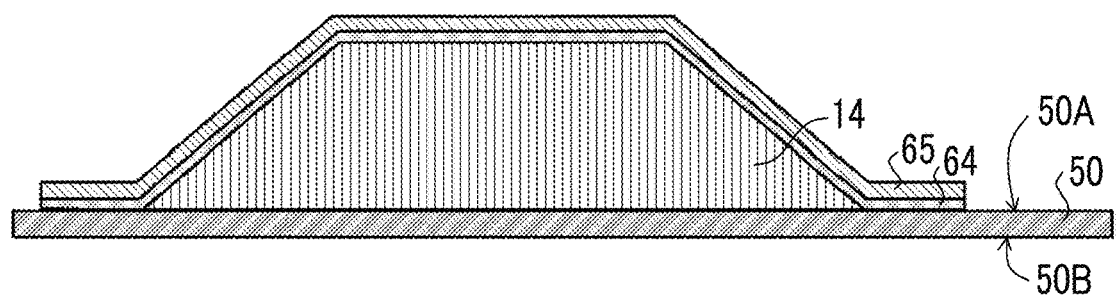
FIG. 5B is a view for explaining an example of the method of manufacturing the radiographic imaging apparatus of the embodiment.

Additionally, as illustrated in FIG. 5B, the conversion layer 14 is formed on the first surface 50A of the fixing plate 50. In the present embodiment, the conversion layer 14 of CsI is directly formed as a columnar crystal on the first surface 50A of the fixing plate 50 by vapor deposition methods, such as a vacuum deposition method, a sputtering method, and a chemical vapor deposition (CVD) method. In this case, the side of the conversion layer 14, which is in contact with the first surface 50A of the fixing plate 50, is a base point side in a growth direction of the columnar crystal.

Additionally, unlike the radiation detector 10 of the present embodiment, GOS ($Gd_2O_2S$:Tb)) or the like may be used as the conversion layer 14 instead of CsI. In this case, for example, the conversion layer 14 is formed by applying a resin in which GOS is dispersed to the fixing plate 50. Additionally, the protective layer 65 is provided on the conversion layer 14 formed on the fixing plate 50 with the adhesive layer 64 interposed therebetween.

In addition, any step may be performed first, regardless of the order of the step of forming the sensor substrate 12 described with reference to FIG. 5A and the step of forming the conversion layer 14 described with reference to FIG. 5B, or both the steps may be performed in parallel.

Figure 5C:
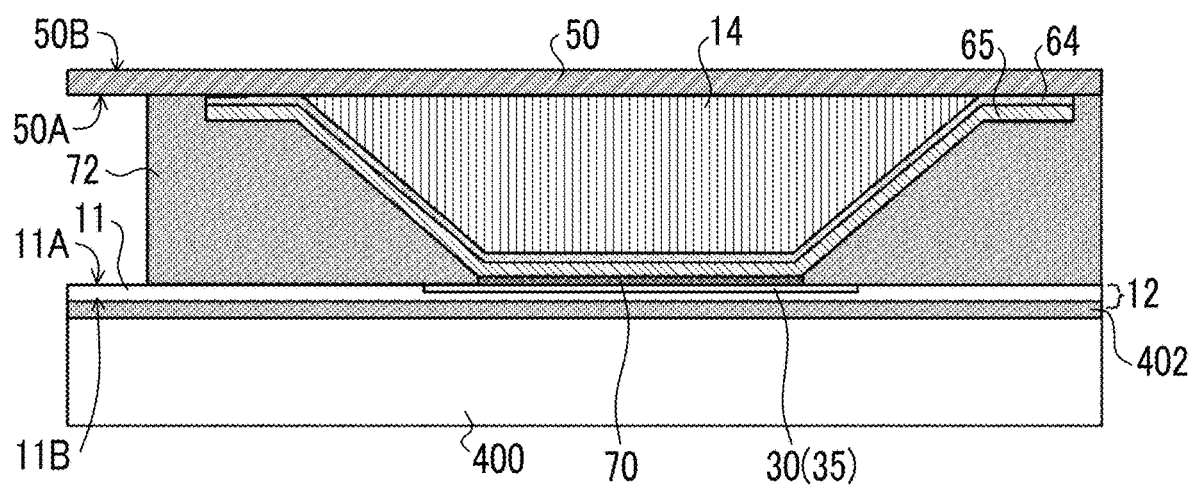
FIG. 5C is a view for explaining an example of the method of manufacturing the radiographic imaging apparatus of the embodiment.

Next, as illustrated in FIG. 5C, the conversion layer 14 is provided on the first surface 11A of the base material 11. In the present embodiment, as described above, the conversion layer 14 is provided on the first surface 11A of the base material 11 by the pressure sensitive adhesive layer 70 in a state where the upper side of the conversion layer 14, more specifically, the side opposite to the side of the conversion layer 14 in contact with the fixing plate 50 faces the first surface 11A of the base material 11 by the pressure sensitive adhesive layer 70.

Additionally, a space between the fixing plate 50 and the sensor substrate 12 is sealed by the sealing member 72. The method of sealing between the fixing plate 50 and the sensor substrate 12 with the sealing member 72 is not particularly limited. For example, after the conversion layer 14 is provided on the sensor substrate 12, the sealing member 72 having fluidity may be injected into the space formed between the sensor substrate 12 and the conversion layer 14 (protective layer 65) to cure the sealing member 72.

Figure 5D:
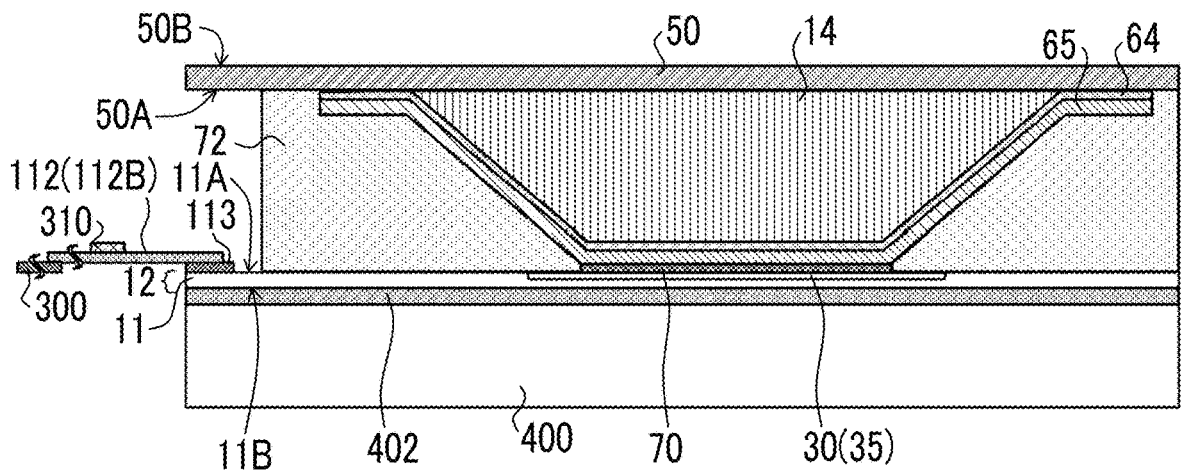
FIG. 5D is a view for explaining an example of the method of manufacturing the radiographic imaging apparatus of the embodiment.

Additionally, as illustrated in FIG. 5D, the flexible cable 112 is electrically connected to the sensor substrate 12. Specifically, first, the terminal 113 is formed on the first surface 11A of the base material 11. Moreover, the flexible cable 112 on which the driving IC 210 or the signal processing IC 310 is mounted is thermocompression bonded to the terminal 113 to electrically connect the terminal 113 and the flexible cable 112. Accordingly, the flexible cable 112 is electrically connected to the sensor substrate 12.

In addition, any step may be performed first regardless of the order of the step of performing the sealing with the sealing member 72 described with reference to FIG. 5C and the step of connecting the flexible cable 112 to the sensor substrate 12 described with reference to FIG. 5D. That is, after the flexible cable 112 is electrically connected to the sensor substrate 12, the space between the sensor substrate 12 and the fixing plate 50 may be sealed by the sealing member 72.

Figure 5E:
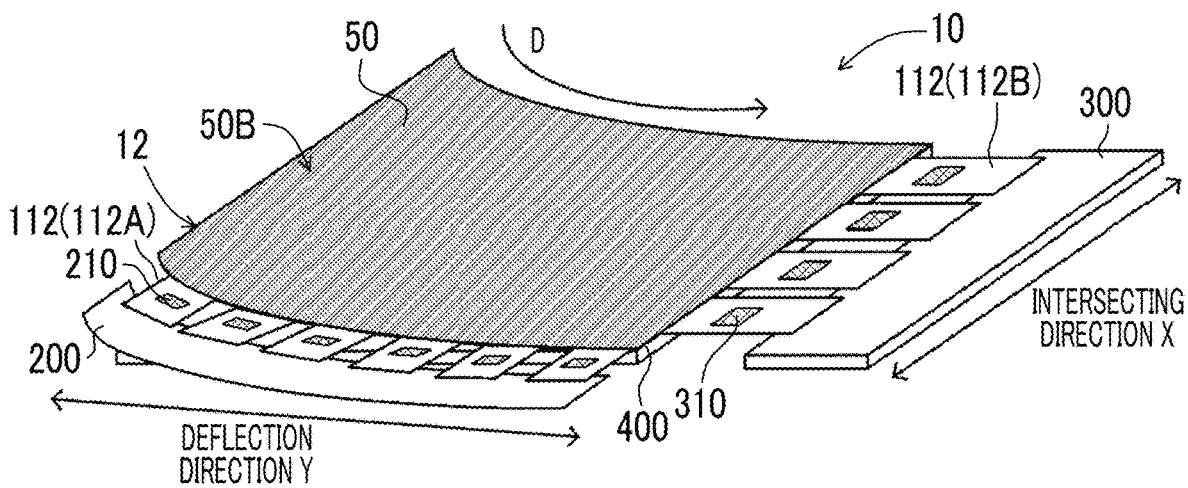
FIG. 5E is a view for explaining an example of the method of manufacturing the radiographic imaging apparatus of the embodiment.

Thereafter, the radiation detector 10 is peeled off from the support body 400 as illustrated in FIG. 5E. In a case where the peeling is performed by mechanical peeling, in the example illustrated in FIG. 5E, the mechanical peeling is performed by setting the side of the base material 11 of the sensor substrate 12 opposite to the side to which the flexible cable 112 is connected as a peeling starting point and gradually pulling the sensor substrate 12 off the support body 400 in the direction of an arrow D illustrated in FIG. 5E from the side to be the starting point toward the side to which the flexible cable 112 is connected, and the radiation detector 10 with the flexible cable 112 connected is obtained.

In addition, it is preferable that the side to be the peeling starting point is a side that intersects the longest side in a case where the sensor substrate 12 is seen in a plan view. In other words, the side in a deflection direction Y in which the deflection is caused by the peeling is preferably the longest side. As an example, in the present embodiment, as illustrated in FIG. 5E, the peeling starting point is the side opposite to the side to which the flexible cable 112B is electrically connected.

Figure 5F:
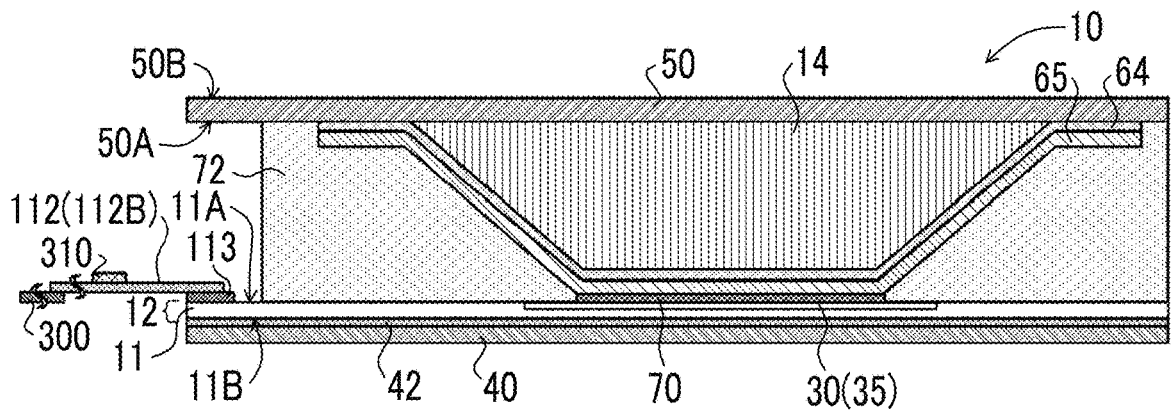
FIG. 5F is a view for explaining an example of the method of manufacturing the radiographic imaging apparatus of the embodiment.

Next, as illustrated in FIG. 5F, the radiation detector 10 of the present embodiment is manufactured by bonding the reinforcing substrate 40 provided with the pressure sensitive adhesive 42 to the second surface 11B of the base material 11.

Figure 5G:
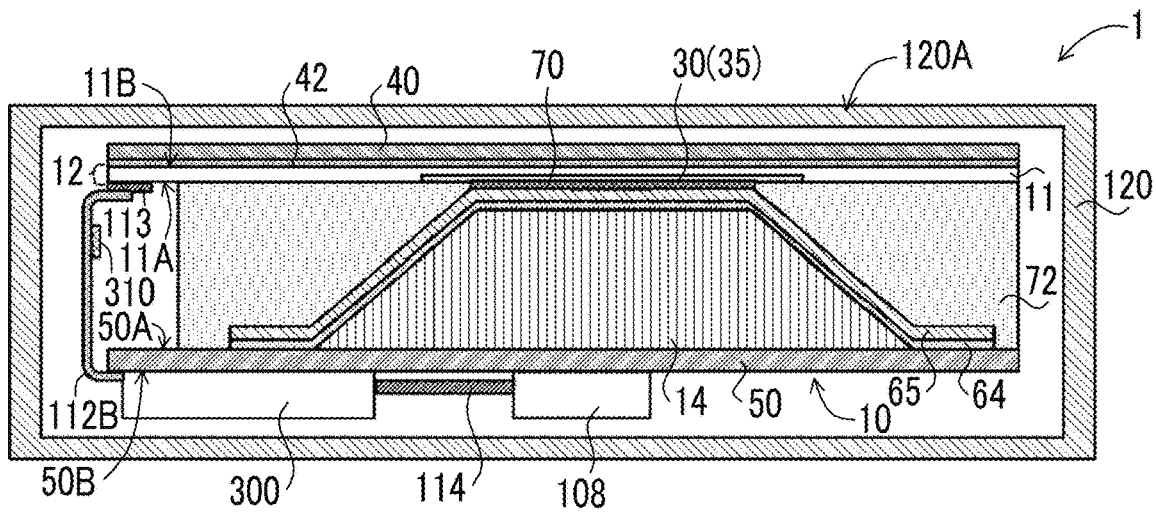
FIG. 5G is a view for explaining an example of the method of manufacturing the radiographic imaging apparatus of the embodiment.

Moreover, as illustrated in FIG. 5G, the circuit unit including the signal processing substrate 300, the driving substrate 200, and the control substrate 110 is fixed to the second surface 50B of the fixing plate 50. Additionally, the radiation detector 10 is housed in the housing 120 in a state where the base material 11 (reinforcing substrate 40) faces the irradiation surface 120A. In this way, the radiographic imaging apparatus 1 of the present embodiment is manufactured.

In addition, the radiographic imaging apparatus 1 and the radiation detector 10 according to the present embodiment may have, for example, the configurations illustrated in the following Modification Examples 1 to 11. In addition, configurations may be adopted in which the respective Modification Examples 1 to 11 are combined appropriately, and the invention is not limited to Modification Examples 1 to 11.

Modification Example 1

Figure 6:
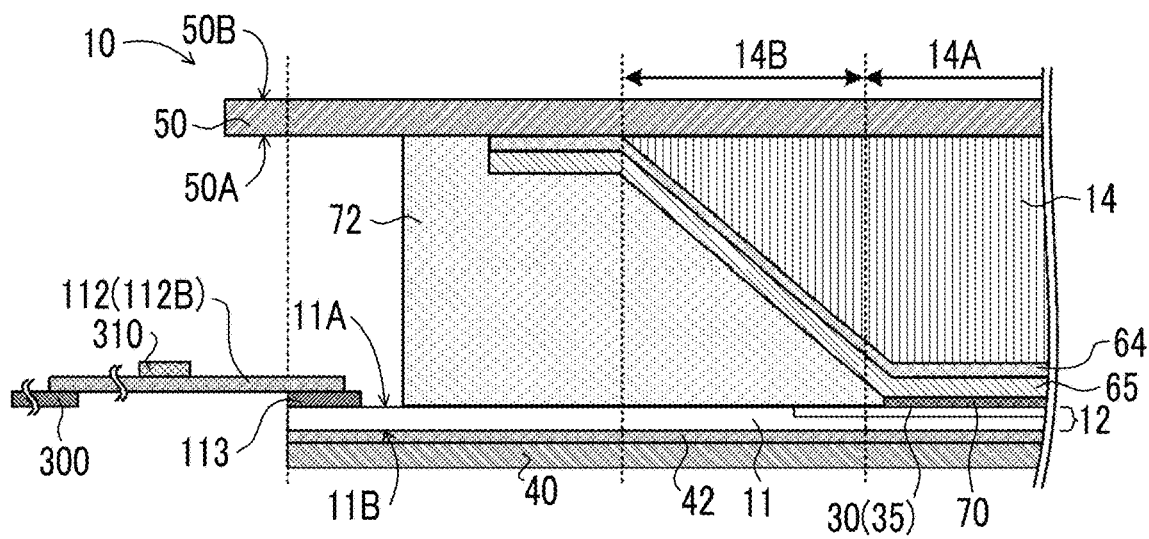
FIG. 6 is a cross-sectional view taken along line A-A of a radiation detector of Modification Example 1.

In the present modification example, a modification example relating to the fixing plate 50 will be described with reference to FIG. 6. FIG. 6 illustrates an example of a cross-sectional view of a radiation detector 10 of the present modification example, which corresponds to the sectional view taken along the line A-A of the radiation detector 10 illustrated in FIG. 3.

In the radiation detector 10 illustrated in FIGS. 2 and 3, the area of the fixing plate 50 is the same as the area of the base material 11. On the other hand, in the radiation detector 10 of the present modification example illustrated in FIG. 6, the area of the fixing plate 50 is larger than the area of the base material 11. Specifically, the area of the first surface 50A of the fixing plate 50 is larger than the area of the first surface 11A of the base material 11. In addition, the specific area of the fixing plate 50 can be determined depending on the size of the inside of the housing 120 that houses the radiation detector 10, and the like. Additionally, as illustrated in FIG. 6, the end part of the fixing plate 50 is located outside the end part of the base material 11, that is, the sensor substrate 12.

In this way, by making the area of the fixing plate 50 larger than the area of the base material 11, for example, in a case where an impact is applied to the housing 120 and a side surface (a surface intersecting the irradiation surface 120A) of the housing 120 is dented such that the radiographic imaging apparatus 1 is dropped, the fixing plate 50 interferes with the side surface of the housing 120. On the other hand, since the sensor substrate 12 has a smaller area than the fixing plate 50, the sensor substrate 12 is less likely to interfere with the side surface of the housing 120. Therefore, according to the radiation detector 10 of the present modification example, it is possible to suppress the influence of the impact applied to the radiographic imaging apparatus 1 on the sensor substrate 12.

In addition, from the viewpoint of suppressing the influence of the impact of the fixing plate 50 applied to the radiographic imaging apparatus 1 on the sensor substrate 12, as illustrated in FIG. 6, at least a portion of the end part of the fixing plate 50 may protrude further outward than the end part of the base material 11. For example, unlike the present modification example, even in a case where the area of the fixing plate 50 is smaller than the area of the base material 11, the end part of the fixing plate 50 that protrudes further outward than the end part of the base material 11 interferes with the side surface of the housing 120. Therefore, the influence of the impact on the sensor substrate 12 can be suppressed similarly to the present modification example.

Modification Example 2

Figure 7:
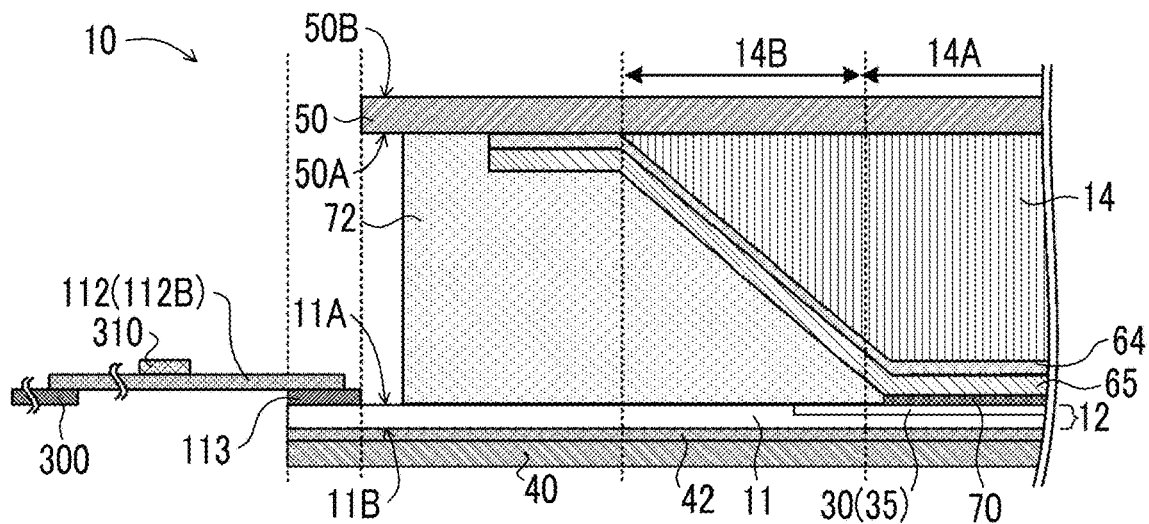
FIG. 7 is a cross-sectional view taken along line A-A of a radiation detector of Modification Example 2.

In the present modification example, a modification example relating to the fixing plate 50 will be described with reference to FIG. 7. FIG. 7 illustrates an example of a cross-sectional view of a radiation detector 10 of the present modification example, which corresponds to the sectional view taken along the line A-A of the radiation detector 10 illustrated in FIG. 3.

In the radiation detector 10 illustrated in FIGS. 2 and 3, the area of the fixing plate 50 is the same as the area of the base material 11. On the other hand, in the radiation detector 10 of the present modification example illustrated in FIG. 7, the area of the fixing plate 50 is smaller than the area of the base material 11. Specifically, the area of the first surface 50A of the fixing plate 50 is smaller than the area of the first surface 11A of the base material 11. In the example illustrated in FIG. 7, the fixing plate 50 is not provided at the position facing the terminal 113. That is, the area of the fixing plate 50 in the radiation detector 10 of the present modification example is smaller than a value obtained by subtracting the area of a region where the terminal 113 is provided from the area of the base material 11.

Removing the flexible cable 112 or a component electrically connected to the base material 11 (sensor substrate 12) and newly reconnecting the component due to a defect or a positional deviation is referred to as rework. In this way, by making the area of the fixing plate 50 smaller than the area of the base material 11, the rework can be performed without being disturbed by the end part of the fixing plate 50. Therefore, the rework of the flexible cable 112 can be facilitated.

Modification Example 3

Figure 8:
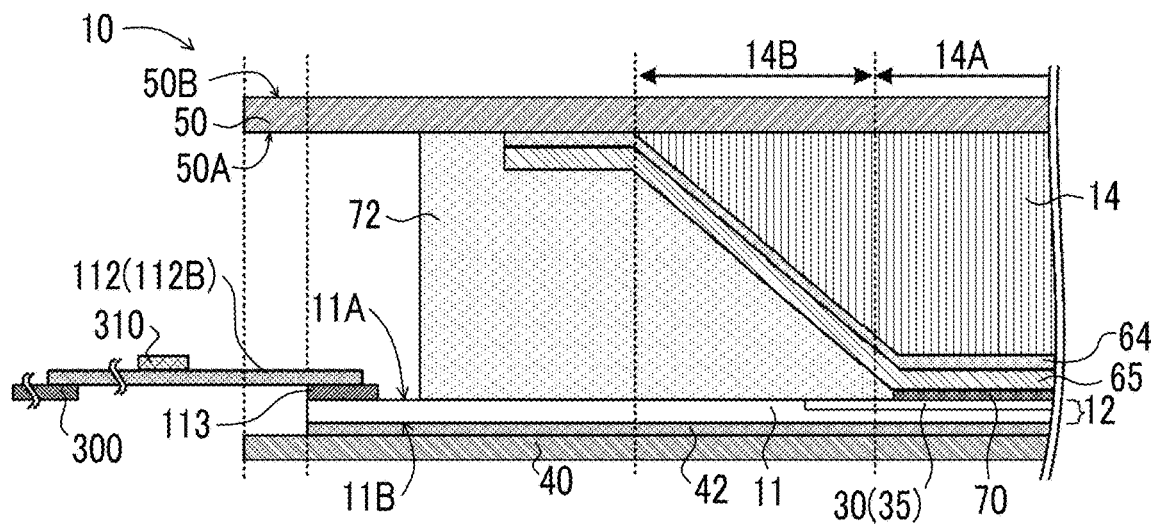
FIG. 8 is a cross-sectional view taken along line A-A of a radiation detector of Modification Example 3.

In the present modification example, a modification example relating to the reinforcing substrate 40 will be described with reference to FIG. 8. FIG. 8 illustrates an example of a cross-sectional view of a radiation detector 10 of the present modification example, which corresponds to the sectional view taken along the line A-A of the radiation detector 10 illustrated in FIG. 3.

In the radiation detector 10 illustrated in FIGS. 2 and 3, the area of the reinforcing substrate 40 is the same as the area of the base material 11. On the other hand, in the radiation detector 10 of the present modification example illustrated in FIG. 8, the area of the reinforcing substrate 40 is larger than the area of the base material 11. In addition, the specific area of the fixing plate 50 can be determined depending on the size of the inside of the housing 120 that houses the radiation detector 10, and the like. Additionally, as illustrated in FIG. 8, the end part of the reinforcing substrate 40 is located outside the end part of the base material 11, that is, the sensor substrate 12.

In addition, in the radiation detector 10 illustrated in FIG. 8, similarly to the radiation detector 10 of the above Modification Example 1, the area of the fixing plate 50 is also larger than the area of the base material 11, and the end part of the fixing plate 50 is located outside the end part of the sensor substrate 12. As an example, in the radiation detector 10 of the present modification example, the positions of the end part of the fixing plate 50 and the end part of the reinforcing substrate 40 are the same, and the length of the fixing plate 50 protruding from the sensor substrate 12 and the length of the reinforcing substrate 40 are the same.

In this way, by making the area of the reinforcing substrate 40 larger than the area of the base material 11, for example, for example, in a case where an impact is applied to the housing 120 and a side surface (a surface intersecting the irradiation surface 120A) of the housing 120 is dented such that the radiographic imaging apparatus 1 is dropped, the reinforcing substrate 40 interferes with the side surface of the housing 120. On the other hand, since the sensor substrate 12 itself has a smaller area than the reinforcing substrate 40, the sensor substrate 12 is less likely to interfere with the side surface of the housing 120. Therefore, according to the radiation detector 10 of the present modification example, it is possible to suppress the influence of the impact applied to the radiographic imaging apparatus 1 on the sensor substrate 12.

Modification Example 4

Figure 9:
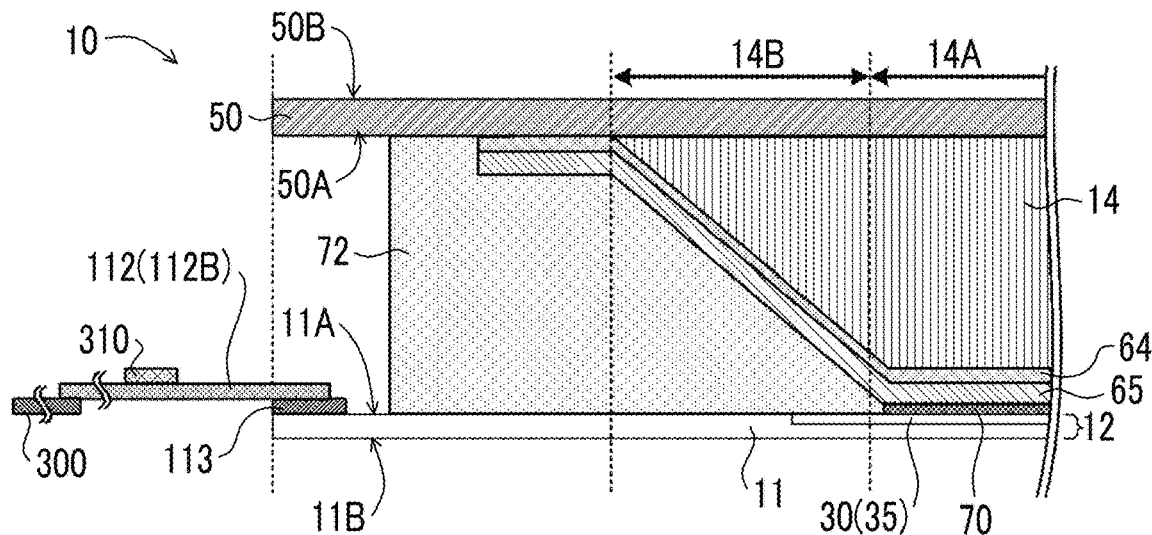
FIG. 9 is a cross-sectional view taken along line A-A of a radiation detector of Modification Example 4.

In the present modification example, a modification example relating to the reinforcing substrate 40 will be described with reference to FIG. 9. FIG. 9 illustrates an example of a cross-sectional view of a radiation detector 10 of the present modification example, which corresponds to the sectional view taken along the line A-A of the radiation detector 10 illustrated in FIG. 3.

The radiation detector 10 illustrated in FIG. 3 comprises the reinforcing substrate 40. On the other hand, the radiation detector 10 of the present modification example illustrated in FIG. 9 does not comprise the reinforcing substrate 40 and the pressure sensitive adhesive 42. Since the radiation detector 10 can be reduced in weight by not comprising the reinforcing substrate 40 in this way, the radiographic imaging apparatus 1 can be further reduced in weight.

Modification Example 5

Figure 10:
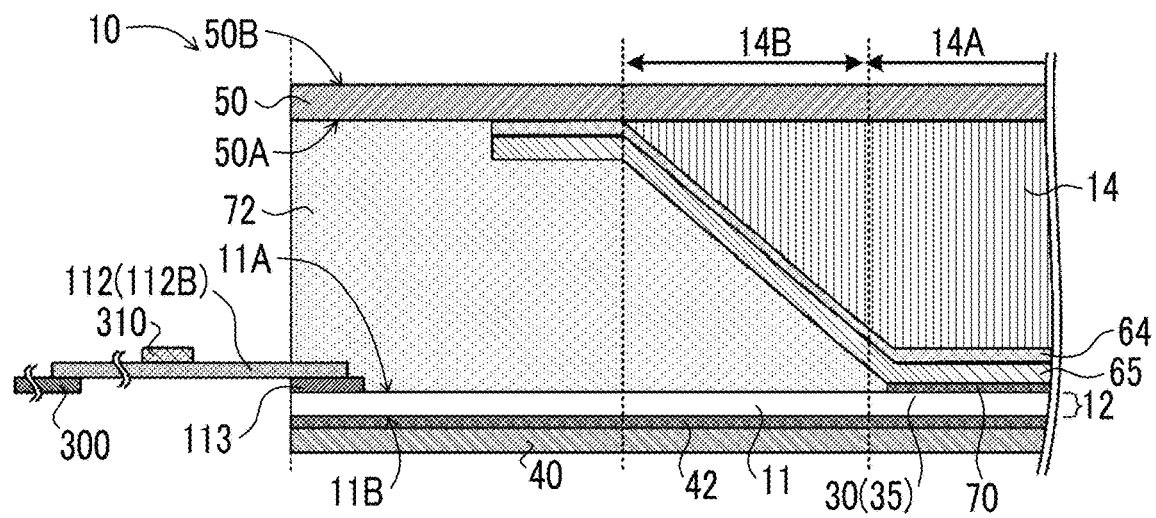
FIG. 10 is a cross-sectional view taken along line A-A of a radiation detector of Modification Example 5.

In the present modification example, a modification example relating to the sealing member 72 will be described with reference to FIG. 10. FIG. 10 illustrates an example of a cross-sectional view of a radiation detector 10 of the present modification example, which corresponds to the sectional view taken along the line A-A of the radiation detector 10 illustrated in FIG. 3.

In the radiation detector 10 illustrated in FIGS. 2 and 3, the sealing member 72 that seals between the sensor substrate 12 and the fixing plate 50 is not provided on the terminal 113 and the flexible cable 112. On the other hand, in the radiation detector 10 of the present modification example illustrated in FIG. 10, the space between the sensor substrate 12 and the fixing plate 50 is sealed by the sealing member 72 up to the end parts of the sensor substrate 12 and the fixing plate 50. Specifically, the space surrounded by the fixing plate 50, the conversion layer 14 (protective layer 65), and the sensor substrate 12 up to the end parts of the sensor substrate 12 and the fixing plate 50 is filled with the sealing member 72. As illustrated in FIG. 10, the sealing member 72 is also provided on the terminal 113 and the flexible cable 112, and the terminal 113 and the flexible cable 112 are covered with the sealing member 72.

In this way, by sealing the space between the sensor substrate 12 and the fixing plate 50 up to the end parts of the sensor substrate 12 and the fixing plate 50 with the sealing member 72, the bending stiffness can be increased up further to the end part of the radiation detector 10. Additionally, it is possible to inhibit the conversion layer 14 from being peeled off from the sensor substrate 12. Moreover, since the sealing member 72 covers the terminal 113 and the flexible cable 112, it is possible to inhibit the flexible cable 112 from being peeled from the terminal 113.

Modification Example 6

Figure 11A:
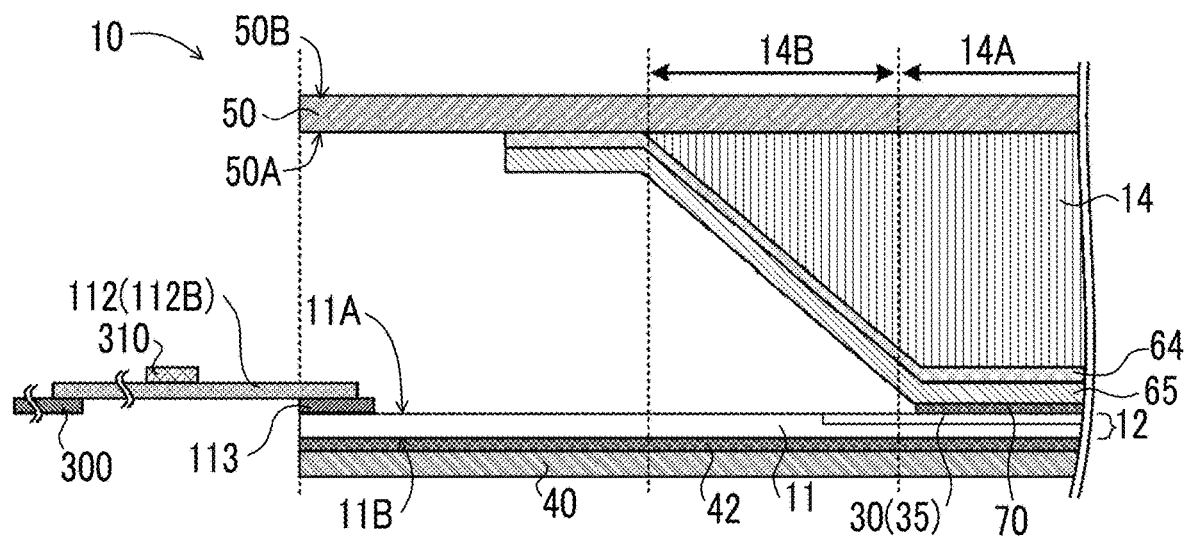
FIG. 11A is a cross-sectional view taken along line A-A of a radiation detector of Modification Example 6.
Figure 11B:
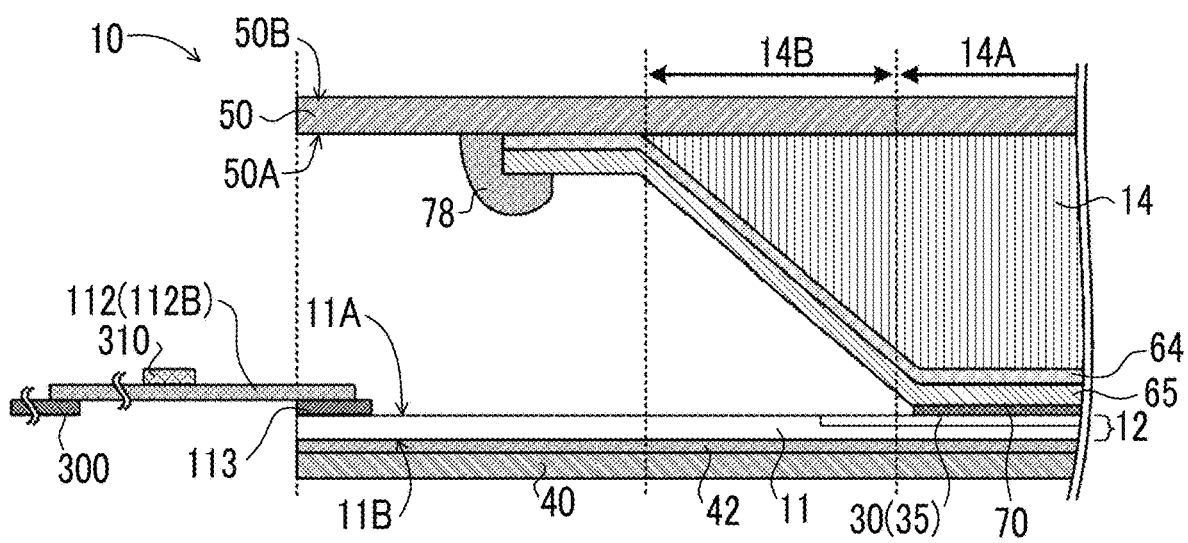
FIG. 11B is a cross-sectional view taken along line A-A of the radiation detector of Modification Example 6.

In the present modification example, a modification example relating to the sealing member 72 will be described with reference to FIGS. 11A and 11B. FIGS. 11A and 11B illustrate an example of a cross-sectional view of a radiation detector 10 of the present modification example, which corresponds to the sectional view taken along the line A-A of the radiation detector 10 illustrated in FIG. 3.

The radiation detector 10 illustrated in FIGS. 2 and 3 comprises the sealing member 72 that seals between the sensor substrate 12 and the fixing plate 50. On the other hand, the radiation detector 10 of the present modification example illustrated in FIG. 11A does not comprise the sealing member 72. That is, the space between the sensor substrate 12 and the fixing plate 50 remains empty. Since the radiation detector 10 can be reduced in weight by not comprising the sealing member 72 in this way, the radiographic imaging apparatus 1 can be further reduced in weight.

Additionally, as illustrated in FIG. 11B, the end parts of the adhesive layer 64 and the protective layer 65 may be sealed by a sealing member 78. The sealing member 78 is preferably provided in a region that extends from the first surface 50A of the fixing plate 50 to the surface of the protective layer 65 and does not cover the pixel region 35. A resin can be used as the material of the sealing member 78, and a thermoplastic resin is particularly preferable. Specifically, acrylic glue, urethane glue, or the like can be used as the sealing member 78. By sealing the end parts of the adhesive layer 64 and the protective layer 65 with the sealing member 78, the peeling of the adhesive layer 64 and the protective layer 65 can be suppressed.

Modification Example 7

The present modification example will be described with reference to FIGS. 12A to 12E. FIGS. 12A to 12E illustrate an example of a cross-sectional view of a radiation detector 10 of the present modification example, which corresponds to the sectional view taken along the line A-A of the radiation detector 10 illustrated in FIG. 3.

Figure 12A:
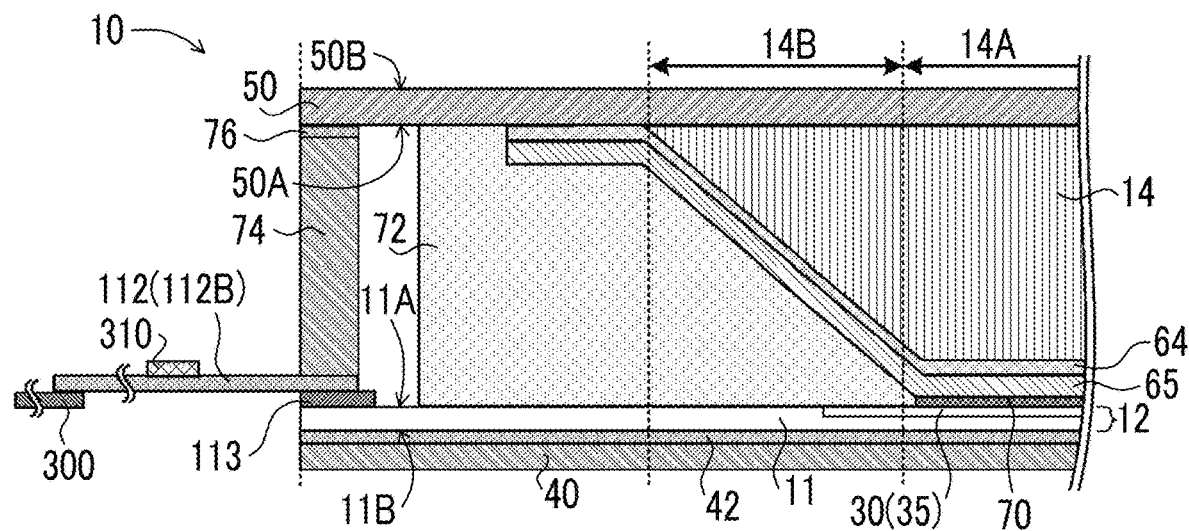
FIG. 12A is a cross-sectional view taken along line A-A of a radiation detector of Modification Example 7.

In the radiation detector 10 of the present modification example illustrated in FIG. 12A, the end part of the fixing plate 50 is supported by a support member 74. That is, one end of the support member 74 is connected to the flexible cable 112 or the first surface 11A of the base material 11, and the other end of the support member 74 is connected to the end part of the first surface 50A of the fixing plate 50 via the adhesive layer 76. In addition, the support member 74 may be provided on the entire outer peripheral part of the sensor substrate 12 or may be provided on a portion of the outer periphery. In this way, by supporting the end part of the fixing plate 50 that extends while forming the space between the conversion layer 14 and the sensor substrate 12 with the support member 74, the conversion layer 14 can be inhibited from being peeled from the sensor substrate 12. Additionally, by providing the support member 74 on the flexible cable 112 and the terminal 113, it is possible to inhibit the flexible cable 112 from being peeled off from the terminal 113.

Figure 12B:
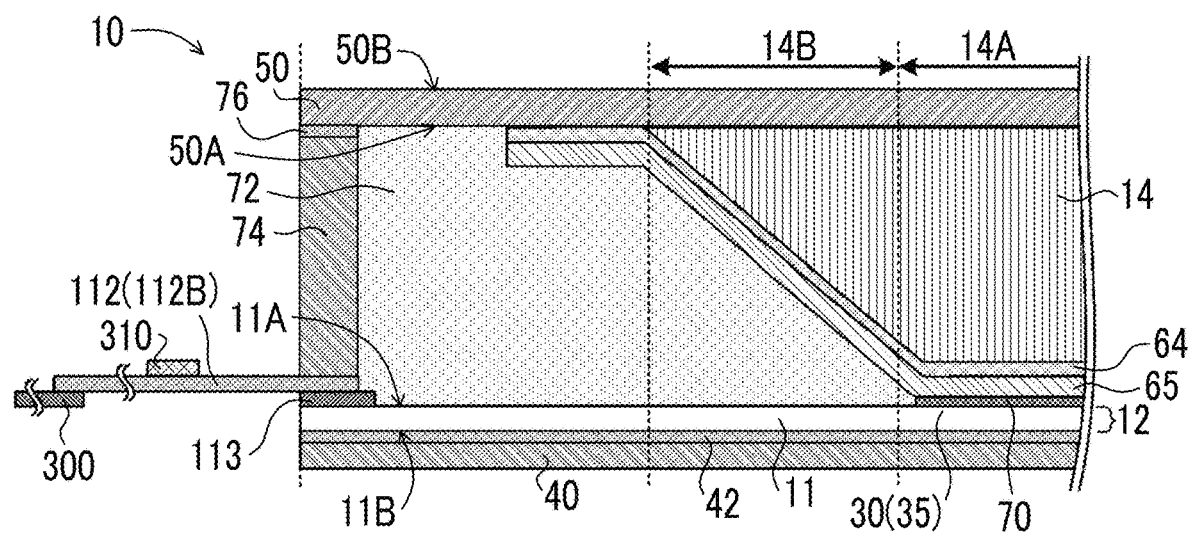
FIG. 12B is a cross-sectional view taken along line A-A of the radiation detector of Modification Example 7.
Figure 12C:
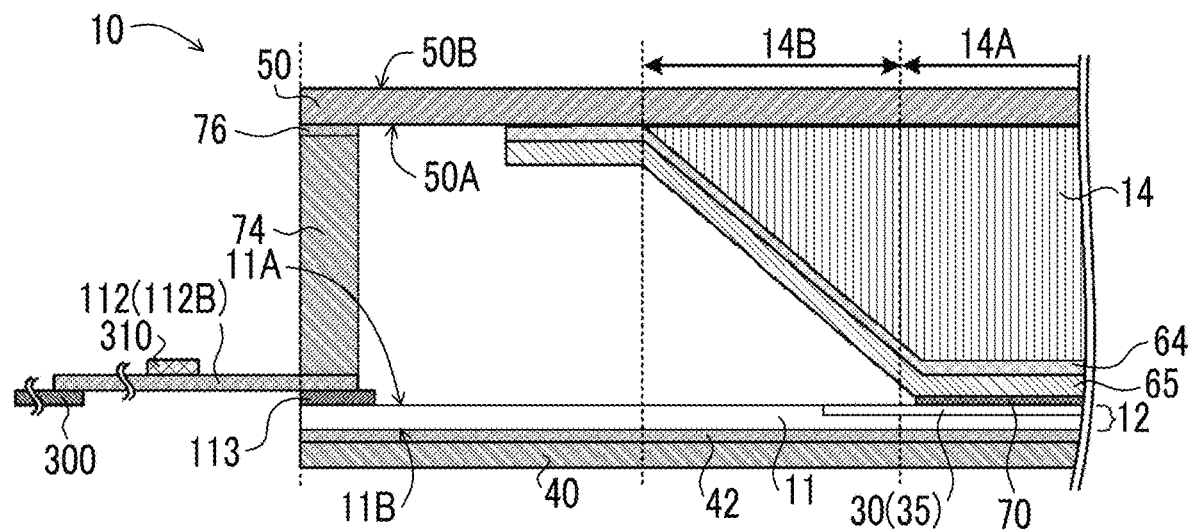
FIG. 12C is a cross-sectional view taken along line A-A of the radiation detector of Modification Example 7.

In addition, as illustrated in FIG. 12B, the entire space surrounded by the support member 74, the fixing plate 50, the conversion layer 14 (protective layer 65), and the sensor substrate 12 may be filled with the sealing member 72 and may be sealed by the sealing member 72. On the other hand, as illustrated in FIG. 12C, a configuration may be adopted in which the radiation detector 10 does not comprise the sealing member 72.

Figure 12D:
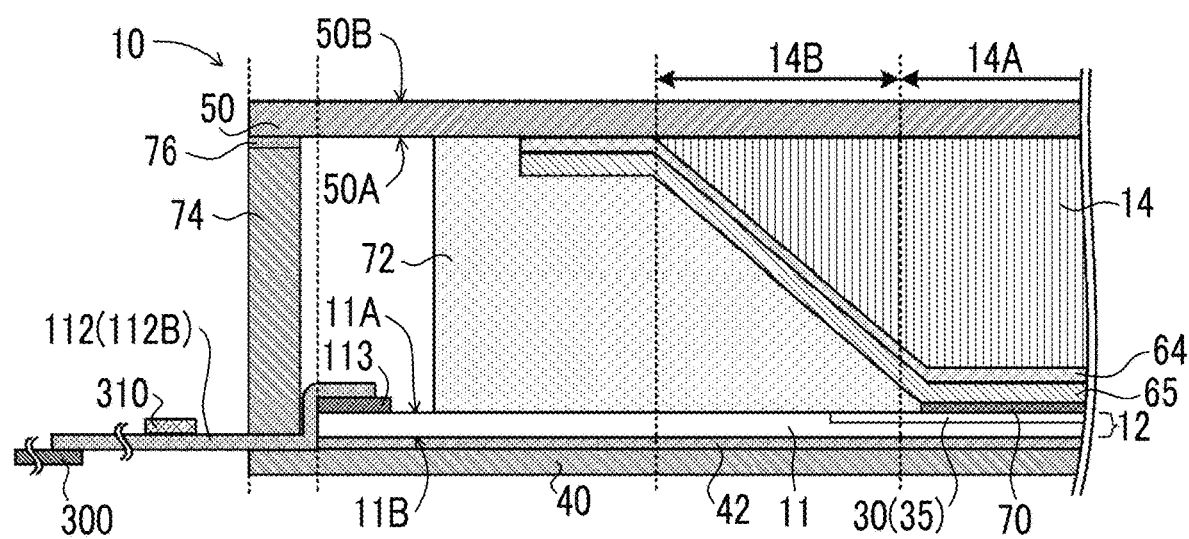
FIG. 12D is a cross-sectional view taken along line A-A of the radiation detector of Modification Example 7.

Additionally, as illustrated in FIG. 12D, the position where the support member 74 is provided may be outside the sensor substrate 12. In the radiation detector 10 illustrated in FIG. 12D, similarly to the same as those of the radiation detector 10 of Modification Example 3, the area of the reinforcing substrate 40 and the fixing plate 50 is larger than that of the base material 11, and the end parts of the reinforcing substrate 40 and the fixing plate 50 are located outside the end part of the base material 11. One end of the support member 74 is connected to the reinforcing substrate 40 or the flexible cable 112, and the other end of the support member 74 is connected to the end part of the first surface 50A of the fixing plate 50 via the adhesive layer 76.

Figure 12E:
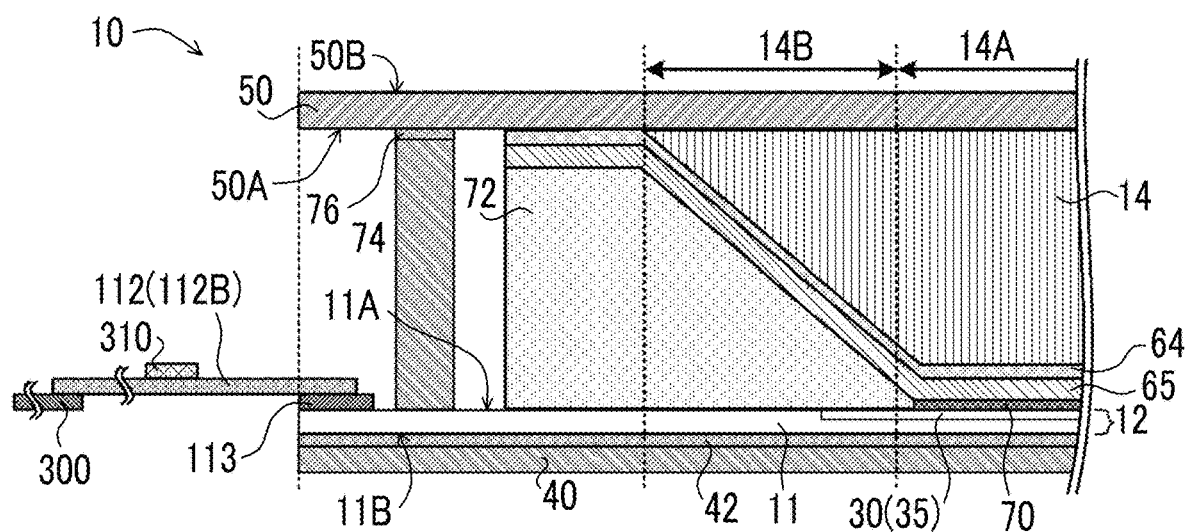
FIG. 12E is a cross-sectional view taken along line A-A of the radiation detector of Modification Example 7.

Additionally, as illustrated in FIG. 12E, the position where the support member 74 is provided may be only outside the region where the flexible cable 112 and the terminal 113 are provided. FIG. 12E illustrates a configuration in which the end part of the fixing plate 50 is indicated by the support member 74 in a region inside the region of the first surface 11A of the base material 11 where the terminal 113 is provided. In the example illustrated in FIG. 12E, one end of the support member 74 is connected to the first surface 11A of the base material 11, and the other end of the support member 74 is connected to the end part of the first surface 50A of the fixing plate 50 via the adhesive layer 76. In this way, by not providing the support member 74 on the flexible cable 112 and the terminal 113, the rework of the flexible cable 112 can be facilitated.

Modification Example 8

Figure 13:
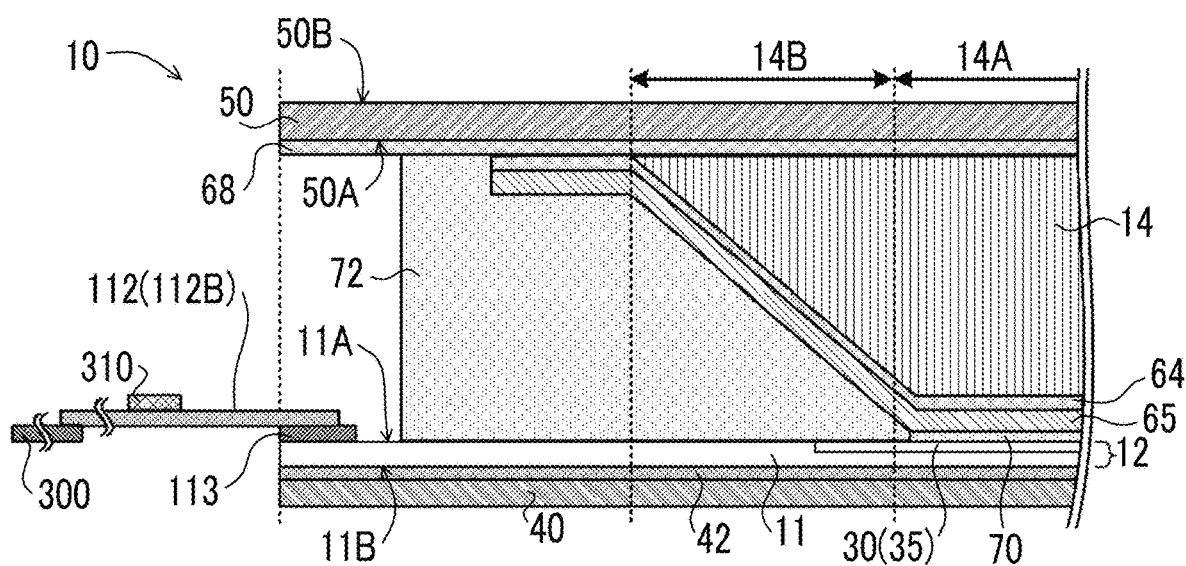
FIG. 13 is a cross-sectional view taken along line A-A of a radiation detector of Modification Example 8.

The present modification example will be described with reference to FIG. 13. FIG. 13 illustrates an example of a cross-sectional view of a radiation detector 10 of the present modification example, which corresponds to the sectional view taken along the line A-A of the radiation detector 10 illustrated in FIG. 3.

As illustrated in FIG. 13, in the radiation detector 10 of the present modification example, a reflective layer 68 is provided between the fixing plate 50 and the conversion layer 14. The reflective layer 68 covers the entire first surface 50A of the fixing plate 50. The reflective layer 68 has a function of reflecting the light converted by the conversion layer 14. The reflective layer 68 is preferably made of a resin material containing a metal or a metal oxide. As the materials of the reflective layer 68, for example, white PET, $TiO_2$, $Al_2O_3$, foamed white PET, specular reflection aluminum, and the like can be used. White PET is obtained by adding a white pigment such as $TiO_2$ or barium sulfate to PET, and foamed white PET is white PET having a porous surface. Additionally, as the material of the reflective layer 68, a laminated film of a resin film and a metal film may be used. Examples of the laminated film of the resin film and the metal film include ALPET (registered trademark) sheets. The thickness of the reflective layer 68 is preferably 10 μm or more and 40 μm or less. In this way, by comprising the reflective layer 68 between the fixing plate 50 and the conversion layer 14, the light converted by the conversion layer 14 can be efficiently guided to the pixels 30 of the sensor substrate 12.

Modification Example 9

Figure 14:
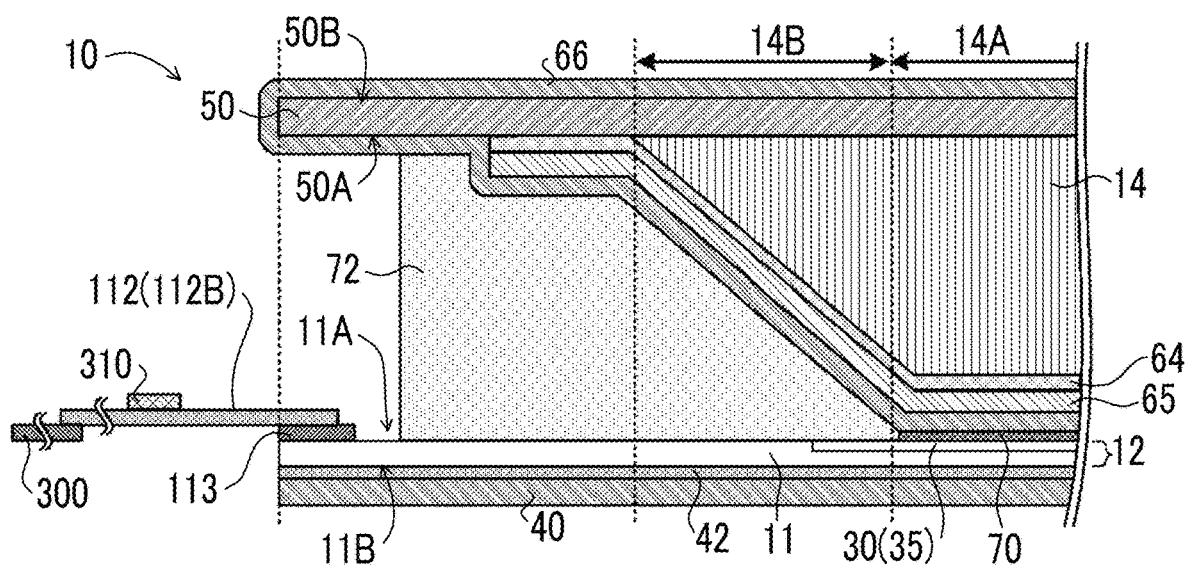
FIG. 14 is a cross-sectional view taken along line A-A of a radiation detector of Modification Example 9.

The present modification example will be described with reference to FIG. 14. FIG. 14 illustrates an example of a cross-sectional view of a radiation detector 10 of the present modification example, which corresponds to the sectional view taken along the line A-A of the radiation detector 10 illustrated in FIG. 3.

As illustrated in FIG. 14, the conversion layer 14 and the fixing plate 50 of the radiation detector 10 of the present modification example are covered with a moistureproof film 66. Specifically, the conversion layer 14 formed on the fixing plate 50 is integrated, and the entirety thereof is covered with the moistureproof film 66.

As the moistureproof film 66, for example, a Parylene (registered trademark) film, an insulating sheet such as polyethylene terephthalate, a laminated film of a resin film and a metal film, or the like is used. Examples of the laminated film of the resin film and the metal film include ALPET (registered trademark) sheets. In this way, by covering the entire fixing plate 50 and the conversion layer 14 with the moistureproof film 66, particularly, until the conversion layer 14 formed on the fixing plate 50 is provided on the sensor substrate 12 in the manufacturing process of the radiographic imaging apparatus 1, it is possible to enhance the moisture-proof property in a case where the conversion layer 14 is handled alone.

Modification Example 10

Figure 15:
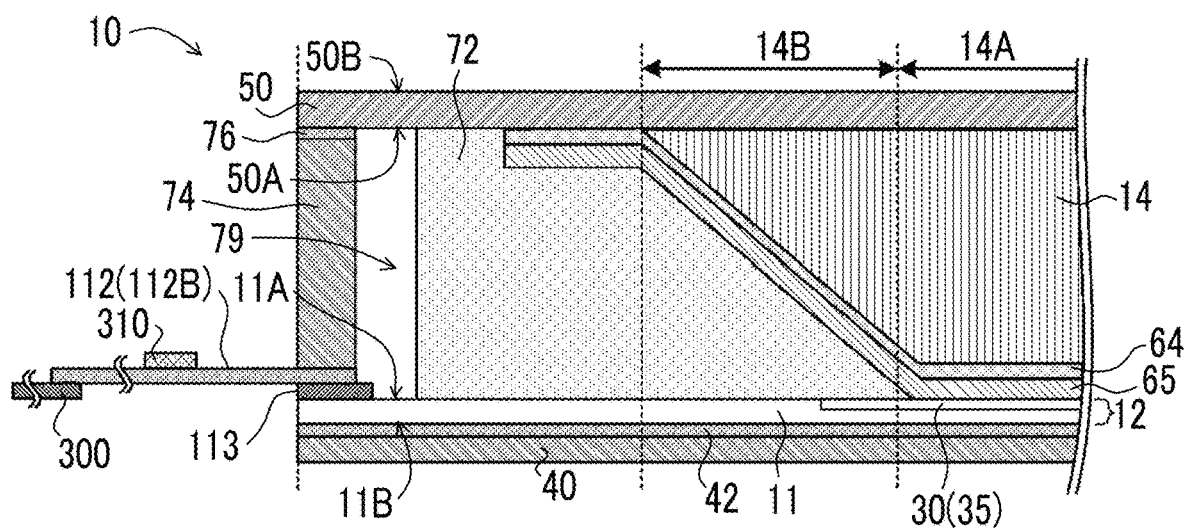
FIG. 15 is a cross-sectional view taken along line A-A of a radiation detector of Modification Example 10.

The present modification example will be described with reference to FIG. 15. FIG. 15 illustrates an example of a cross-sectional view of a radiation detector 10 of the present modification example, which corresponds to the sectional view taken along the line A-A of the radiation detector 10 illustrated in FIG. 3.

FIG. 15 illustrates the radiation detector 10 in which the step of providing the conversion layer 14 on the first surface 11A of the base material 11 in the manufacturing method is manufactured by a method different from the method described with reference to FIG. 5C. Additionally, in the method of manufacturing the radiation detector 10 illustrated in FIG. 15, the timing at which the flexible cable 112 is electrically connected to the sensor substrate 12 is different from the timing described with reference to FIG. 5D.

Moreover, in the method of manufacturing the radiation detector 10 illustrated in FIG. 15, before the conversion layer 14 is provided on the first surface 11A of the base material 11, the terminal 113 is formed on the first surface 11A of the base material 11 and the terminal 113 and the flexible cable 112 are electrically connected. Moreover, the support member 74 is provided on the flexible cable 112. In addition, the support member 74 may be provided on the first surface 50A of the fixing plate 50. Additionally, an uncured sealing member 72 is provided in a region extending from the peripheral edge part 14B of the conversion layer 14 formed on the fixing plate 50 to the first surface 50A of the fixing plate 50. The conversion layer 14 formed on the fixing plate 50 and provided with the uncured sealing member 72 is disposed on the first surface 11A of the base material 11.

In this state, an internal space 79 formed by the base material 11, the fixing plate 50, the sealing member 72, and the support member 74 is pressure-reduced to, for example, a pressure, such as 0.2 atm to 0.5 atm, which is lower than the atmospheric pressure, using a pressure-reducing pump or the like. In this way, by making the internal space 79 formed by the base material 11, the fixing plate 50, the sealing member 72, and the support member 74 lower than the atmospheric pressure, the base material 11 (sensor substrate 12) and the fixing plate 50 are pressed from the outside to the internal space 79 side at the atmospheric pressure. In the method of manufacturing the radiation detector 10 of the present modification example, the conversion layer 14 is provided on the first surface 11A of the base material 11 in this way.

In the radiation detector 10 of the present modification example, the conversion layer 14 is provided on the first surface 11A of the base material 11 by pressing the base material 11 and the fixing plate 50 at the atmospheric pressure. Therefore, as illustrated in FIG. 15, the conversion layer 14 and the base material 11 closely adhere to each other without providing the pressure sensitive adhesive layer 70.

Modification Example 11

Figure 16A:
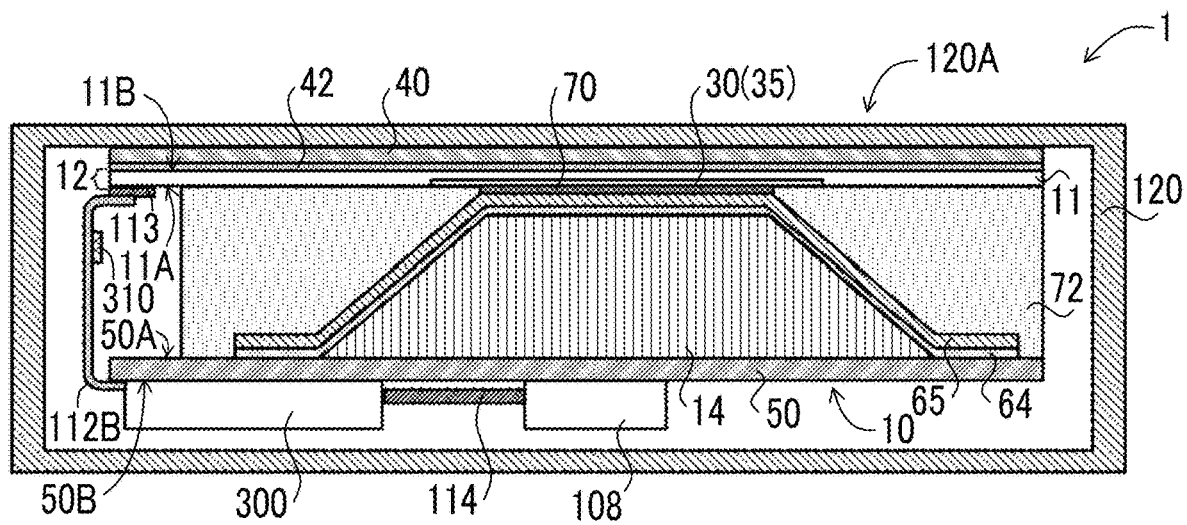
FIG. 16A is a cross-sectional view of a radiographic imaging apparatus of Modification Example 11.
Figure 16B:
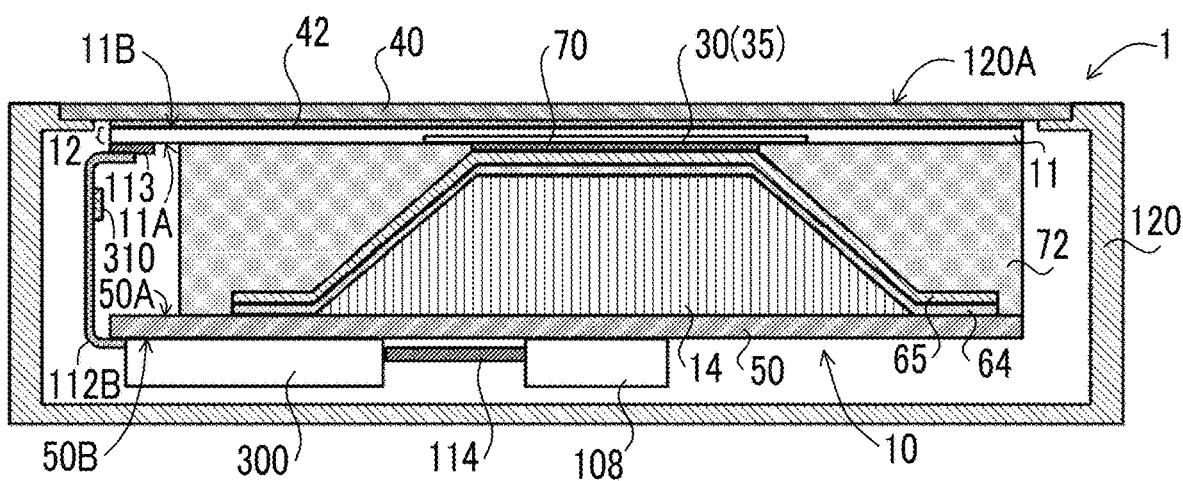
FIG. 16B is a cross-sectional view of the radiographic imaging apparatus of Modification Example 11.

In the present modification example, a modification example, in a housed state, of the radiation detector 10 in the radiographic imaging apparatus 1 will be described with reference to FIGS. 16A and 16B. FIGS. 16A and 16B are examples of cross-sectional views of a radiographic imaging apparatus 1 of the present modification example.

In the radiographic imaging apparatus 1 illustrated in FIG. 4, a space is provided between the top plate on the irradiation surface 120A side of the housing 120 and the reinforcing substrate 40. On the other hand, in the radiographic imaging apparatus 1 of the present modification example illustrated in FIG. 16A, the reinforcing substrate 40 is in contact with an inner wall surface of the top plate on the irradiation surface 120A side of the housing 120. In this case, the radiation detector 10 and the inner wall surface of the housing 120 may be bonded to each other via an adhesive layer, or may simply be in contact with each other without an adhesive layer. Since the radiation detector 10 and the inner wall surface of the housing 120 are in contact with each other in this way, the stiffness of the radiation detector 10 is further secured.

Additionally, in the radiographic imaging apparatus 1 of the present modification example illustrated in FIG. 16B, the reinforcing substrate 40 is adopted as the top plate on the irradiation surface 120A side of the housing 120. In this case, as illustrated in FIG. 16B, the area of the reinforcing substrate 40 is larger than the area of the sensor substrate 12, and the end part of the reinforcing substrate 40 protrudes further outward than the end part of the sensor substrate 12. In the radiographic imaging apparatus 1 illustrated in FIG. 16B, the radiation detector 10 is housed inside the housing 120 by fitting the reinforcing substrate 40 into an opening portion of the housing 120 that has an opening on a top plate portion on the irradiation surface 120A side. In this way, by using the reinforcing substrate 40 of the radiation detector 10 as the top plate of the housing 120, the thickness of the housing 120, more specifically, the thickness in a radiation transmission direction can be further reduced, and the radiographic imaging apparatus 1 can be slimmed Additionally, since the top plate of the housing 120 itself is unnecessary, the weight of the radiographic imaging apparatus 1 can be further reduced.

The method of manufacturing the radiographic imaging apparatus 1 according to the present embodiment may be, for example, a configuration illustrated in the following Modification Example 12.

Modification Example 12

In the present modification example, a modification example of the method of manufacturing the radiographic imaging apparatus 1 will be described with reference to FIGS. 17A to 17D.

The manufacturing method of the radiographic imaging apparatus 1 of the present modification example is the same as the above-described manufacturing method in the steps described with reference to FIGS. 5A to 5D and is different from the above-described manufacturing method in the subsequent steps. In the present modification example, a step illustrated in FIG. 17A is performed after the step illustrated in FIG. 5D.

Figure 17A:
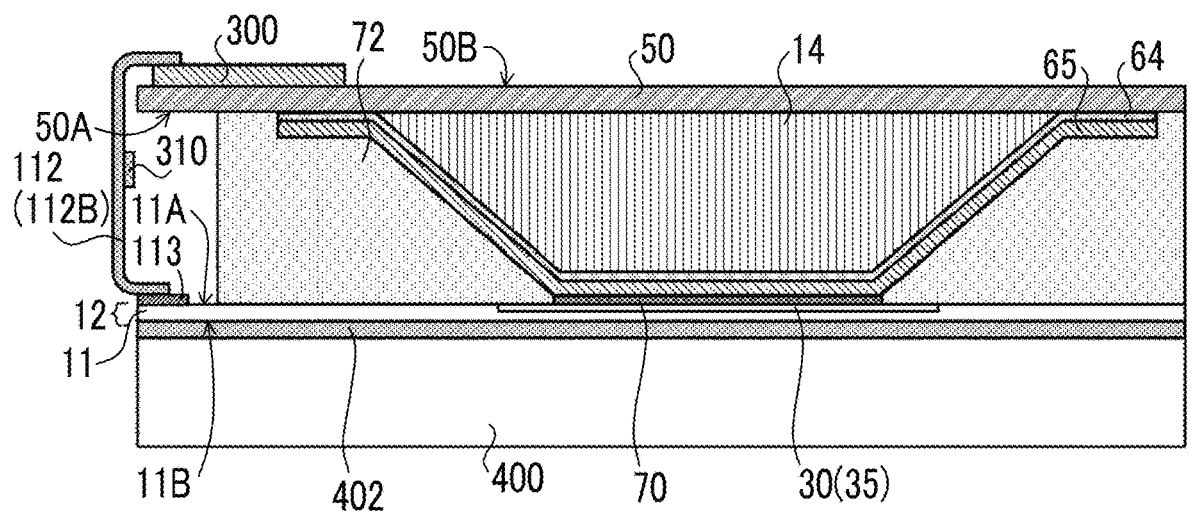
FIG. 17A is a view illustrating an example of a method of manufacturing a radiographic imaging apparatus of Modification Example 12.

As illustrated in FIG. 17A, the other end of the flexible cable 112 is fixed to the second surface 50B of the fixing plate 50. Specifically, the other end of the flexible cable 112A is electrically connected to the driving substrate 200. Additionally, the other end of the flexible cable 112B is electrically connected to the signal processing substrate 300. Moreover, the flexible cable 112 connected to the sensor substrate 12 is folded back to the second surface 50B side of the fixing plate 50, and each of the driving substrate 200 and the signal processing substrate 300 is fixed to the second surface 50B of the fixing plate 50 by a fastening screw. By fixing each of the driving substrate 200 and the signal processing substrate 300 to the second surface 50B of the fixing plate 50, the other end of the flexible cable 112 is fixed to the second surface 50B of the fixing plate 50.

Figure 17B:
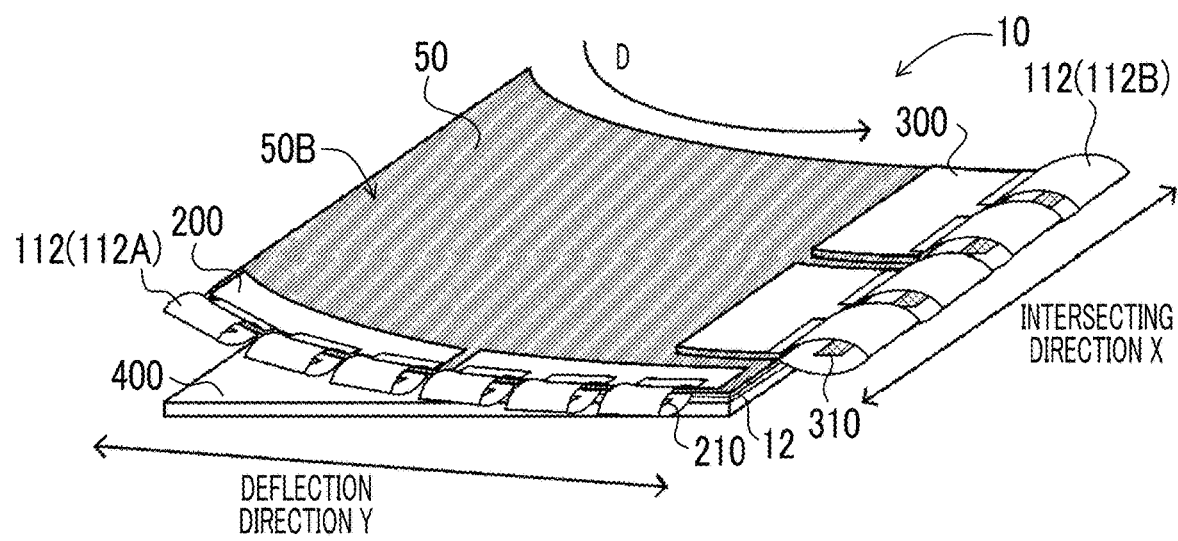
FIG. 17B is a view illustrating an example of the method of manufacturing a radiographic imaging apparatus according to Modification Example 12.

Thereafter, as illustrated in FIG. 17B, with the other end of the flexible cable 112 fixed to the second surface 50B of the fixing plate 50, the radiation detector 10 is peeled from the support body 400 similarly to as the step described with reference to FIG. 5E.

Figure 17C:
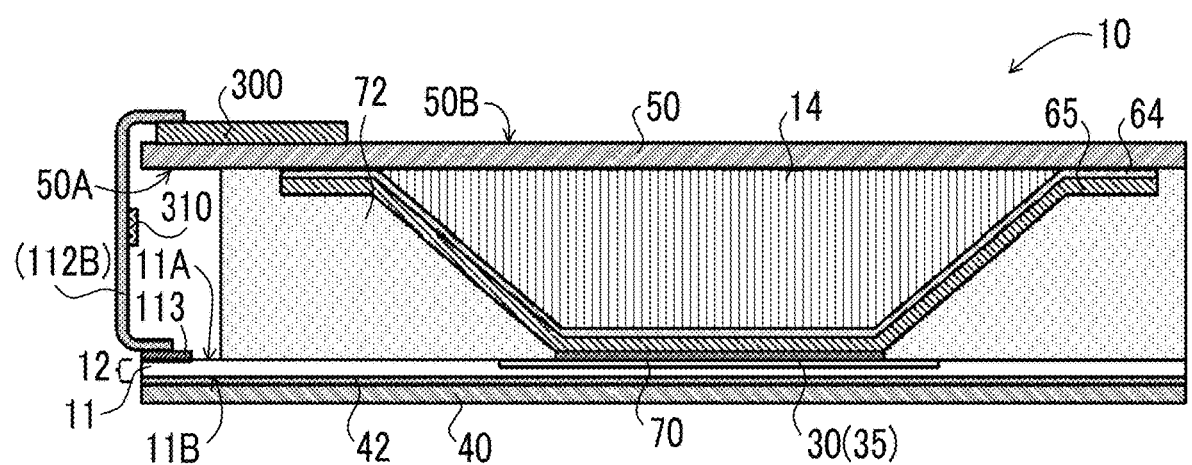
FIG. 17C is a view illustrating an example of the method of manufacturing a radiographic imaging apparatus according to Modification Example 12.

Next, as illustrated in FIG. 17C, the radiation detector 10 of the present embodiment is manufactured by bonding the reinforcing substrate 40 provided with the pressure sensitive adhesive 42 to the second surface 11B of the base material 11.

Figure 17D:
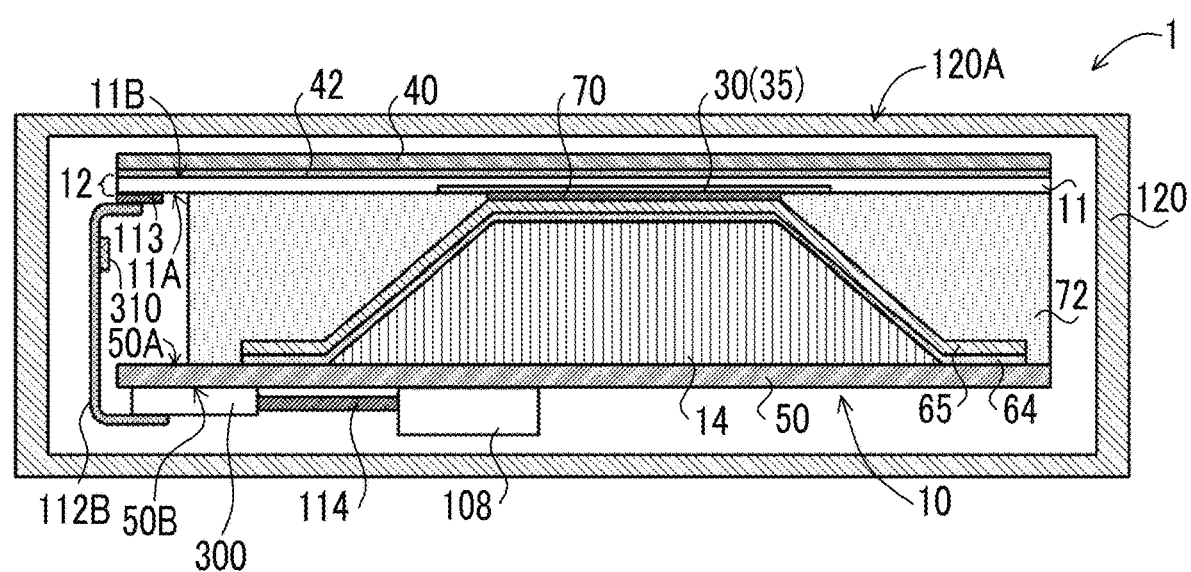
FIG. 17D is a view illustrating an example of a method of manufacturing a radiographic imaging apparatus according to Modification Example 12.

Moreover, as illustrated in FIG. 17D, the radiation detector 10 is housed in the housing 120 in a state where the base material 11 (reinforcing substrate 40) faces the irradiation surface 120A. In this way, the radiographic imaging apparatus 1 of the present embodiment is manufactured.

In the manufacturing process of the radiographic imaging apparatus 1, in a case where the sensor substrate 12 is peeled from the support body 400, the base material 11 is easily deflected. Therefore, the sensor substrate 12 is deflected. The flexible cable 112 may be pulled in a case where the sensor substrate 12 is deflected. For example, since the driving IC 210 or the signal processing IC 310 is mounted on the flexible cable 112, the flexible cable 112 may be pulled depending on the weight of the ICs. Additionally, in a case where the other end of the flexible cable 112 is connected to the circuit unit of the driving substrate 200, the signal processing substrate 300, or the like, the flexible cable 112 is easily pulled depending on the weight of the circuit unit. In a case where the flexible cable 112 is pulled, the position of the flexible cable 112 connected to the sensor substrate 12 may deviate. In this way, in a case where the position of the flexible cable 112 deviates with respect to the sensor substrate 12, there is a concern that a problem may occur in the connection between the flexible cable 112 and the terminal 113. Additionally, as the flexible cable 112 is pulled, the end part of the sensor substrate 12 in the vicinity of the terminal 113 may be distorted. For that reason, the flexible cable 112 may be reworked or the radiographic imaging apparatus 1 may be remanufactured.

In contrast, as described above, in the method of manufacturing the radiographic imaging apparatus 1 according to the present modification example, the flexible cable 112 is fixed to the fixing plate 50 before the sensor substrate 12 is peeled from the support body 400. Then, with the flexible cable 112 fixed to the fixing plate 50, the sensor substrate 12 is peeled from the support body 400. Since the flexible cable 112 is fixed to the fixing plate 50, it is possible to inhibit the flexible cable 112 from being pulled in a case where the support body 400 is peeled from the sensor substrate 12. For that reason, according to the method of manufacturing the radiographic imaging apparatus 1 of the present modification example, in a case where the sensor substrate 12 is deflected during the manufacture of the radiographic imaging apparatus 1, a problem caused by the flexible cable 112 connected to the sensor substrate 12 can be suppressed.

In addition, in the present modification example, a configuration has been described in which the flexible cable 112 is fixed to the fixing plate 50 by fixing the signal processing substrate 300, to which the flexible cable 112 is connected, to the second surface 50B of the fixing plate 50. However, the method of connecting the flexible cable 112 to the fixing plate 50 is not limited to the present embodiment. For example, the flexible cable 112 may be directly fixed to the second surface 50B of the fixing plate 50, the sensor substrate 12 may be peeled from the support body 400, and then the flexible cable 112 may be connected to the driving substrate 200 or the signal processing substrate 300. Additionally, for example, the flexible cable 112 may be fixed to the first surface 50A of the fixing plate 50, the sensor substrate 12 may be peeled from the support body 400, and then the flexible cable 112 may be peeled from the first surface 50A of the fixing plate 50. In this case, the flexible cable 112 peeled from the fixing plate 50 may be connected to the driving substrate 200 or the signal processing substrate 300, and then the driving substrate 200 or the signal processing substrate 300 may be fixed to the fixing plate 50.

As described above, each of the above respective radiographic imaging apparatuses 1 comprises the sensor substrate 12, the circuit unit, the fixing plate 50, the conversion layer 14, and the housing 120. In the sensor substrate 12, the pixel region 35 of the flexible base material 11 is provided with the plurality of pixels 30 for accumulating the electrical charges generated depending on the light converted from radiation. The circuit unit includes at least one of the driving substrate 200, the signal processing substrate 300, or the control substrate 110, and is electrically connected to the sensor substrate 12. The fixing plate 50 fixes the circuit unit. The conversion layer 14 is provided on the first surface 50A opposite to the second surface 50B of the fixing plate 50 on which the circuit unit is fixed, and is provided in a state where the second surface 11B opposite to the fixing plate 50 side is provided faces the first surface 11A of the base material 11 on which the pixels 30 are provided, and converts radiation into light. The housing 120 houses the sensor substrate 12, the circuit unit, the fixing plate 50, and the conversion layer 14.

In this way, in each of the above radiographic imaging apparatuses 1, the conversion layer 14 of the radiation detector 10 is formed on the fixing plate 50 to which the circuit unit for reading out the electrical charges from the pixels 30 is fixed. In other words, the radiation detector 10 comprises the conversion layer 14 formed by using the fixing plate 50 instead of the substrate.

According to the radiographic imaging apparatus 1, since the bending stiffness can be increased by the fixing plate 50 and a desired bending stiffness can be obtained, the impact resistance can be improved. Additionally, according to the radiographic imaging apparatus 1, the weight can be reduced and the thickness can be reduced as compared to a case where the fixing plate 50 is separately provided from the conversion layer 14 formed on the vapor deposition substrate, the support substrate, or the like. Therefore, according to the radiographic imaging apparatus 1, the bending stiffness can be increased and the weight can be reduced.

In addition, the radiographic imaging apparatus 1, the radiation detector 10, and the method of manufacturing the radiographic imaging apparatus 1 are not limited to the configurations described with reference to FIGS. 1 to 17D. For example, as illustrated in FIG. 1, an aspect in which the pixels 30 are two-dimensionally arranged in a matrix has been described. However, the invention is not limited, and the pixels 30 may be one-dimensionally arranged or may be arranged in a honeycomb arrangement. Additionally, the shape of the pixels is also not limited, and may be a rectangular shape, or may be a polygonal shape, such as a hexagonal shape. Moreover, the shape of the pixel region 35 is also not limited.

In addition, the configurations, manufacturing methods, and the like of the radiographic imaging apparatuses, the radiation detectors 10, and the like in the above embodiments and respective modification examples are merely examples, and can be modified in accordance with situations without departing from the scope of the present invention.

Explanation of References

What is claimed is:

1. A radiographic imaging apparatus comprising:
    a substrate in which a plurality of pixels for accumulating electrical charges generated depending on light converted from radiation is provided in a pixel region of a flexible base material;
    a circuit unit that is electrically connected to the substrate;
    a conversion layer that is provided on a surface of the base material on which the pixels are provided, and converts the radiation into light;
    a fixing plate that includes a first surface provided at a surface of the conversion layer that is opposite to which the circuit unit is fixed, and a second surface that fixes the circuit unit; and
    a housing that houses the substrate, the circuit unit, the fixing plate, and the conversion layer,
    wherein an area of the fixing plate is larger than an area of the base material.

2. The radiographic imaging apparatus according to claim 1,
    wherein at least a portion of an end part of the fixing plate protrudes further outward than an end part of the base material.

3. The radiographic imaging apparatus according to claim 1, further comprising:
    a reinforcing substrate that is provided on a surface opposite to the surface of the base material on which the pixels are provided and has a higher stiffness than the base material.

4. The radiographic imaging apparatus according to claim 3,
    wherein the reinforcing substrate is a top plate on a surface of the housing irradiated with the radiation.

5. The radiographic imaging apparatus according to claim 3, further comprising:
    a support member that supports an end part of the fixing plate and an end part of the reinforcing substrate.

6. The radiographic imaging apparatus according to claim 1, further comprising:
    a support member that supports an end part of the fixing plate and an end part of the substrate.

7. The radiographic imaging apparatus according to claim 1,
    wherein a space between the fixing plate and the substrate is sealed with a sealing member.

8. The radiographic imaging apparatus according to claim 1, further comprising:
    a pressure sensitive adhesive layer for providing the conversion layer on the surface of the base material on which the pixels are provided.

9. The radiographic imaging apparatus according to claim 1,
    wherein a surface of the conversion layer opposite to the fixing plate and the surface of the base material on which the pixels are provided are in contact with each other.

10. The radiographic imaging apparatus according to claim 1,
    wherein a main component of a material of the fixing plate is carbon.

11. The radiographic imaging apparatus according to claim 1, wherein the housing houses the substrate, the conversion layer, the fixing plate, and the circuit unit in an arrangement order from a side irradiated with the radiation.

* * * * *